(12) United States Patent
Barbas, III et al.

(10) Patent No.: US 7,067,617 B2
(45) Date of Patent: Jun. 27, 2006

(54) ZINC FINGER BINDING DOMAINS FOR NUCLEOTIDE SEQUENCE ANN

(75) Inventors: Carlos F. Barbas, III, Solana Beach, CA (US); Birgit Dreier, Adlikon (CH)

(73) Assignee: The Scripps Research Institute, La Jolla, CA (US)

( * ) Notice: Subject to any disclaimer, the term of this patent is extended or adjusted under 35 U.S.C. 154(b) by 115 days.

(21) Appl. No.: 10/080,100

(22) Filed: Feb. 21, 2002

(65) Prior Publication Data

US 2002/0165356 A1    Nov. 7, 2002

Related U.S. Application Data

(60) Provisional application No. 60/367,356, filed on Feb. 21, 2001.

(51) Int. Cl.
  C07K 19/00    (2006.01)
  C07K 14/00    (2006.01)
(52) U.S. Cl. .................. 530/300; 530/324; 530/350
(58) Field of Classification Search ................ 530/300, 530/324, 350
  See application file for complete search history.

(56) References Cited

U.S. PATENT DOCUMENTS

| | | |
|---|---|---|
| 4,990,607 A | 2/1991 | Katagiri et al. |
| 5,096,815 A | 3/1992 | Ladner et al. |
| 5,223,409 A | 6/1993 | Ladner et al. |
| 5,243,041 A | 9/1993 | Fernandez-Pol |
| 5,324,638 A | 6/1994 | Tao et al. |
| 5,324,818 A | 6/1994 | Nabel et al. |
| 5,340,739 A | 8/1994 | Stevens et al. |
| 5,350,840 A | 9/1994 | Call et al. |
| 5,376,530 A | 12/1994 | De The et al. |
| 5,403,484 A | 4/1995 | Ladner et al. |
| 5,597,693 A | 1/1997 | Evans et al. |
| 5,639,592 A | 6/1997 | Evans et al. |
| 5,789,538 A | 8/1998 | Rebar et al. |
| 6,140,081 A | 10/2000 | Barbas |
| 2002/0081614 A1 | 6/2002 | Case CC |

FOREIGN PATENT DOCUMENTS

| | | |
|---|---|---|
| WO | WO 95/19431 | 1/1995 |
| WO | WO 96/06166 | 2/1996 |

OTHER PUBLICATIONS

Nagase et al, DNA Research, 2000, vol. 7, pp. 271-281.*
Zweidler-McKay, et al., "Gfi-1 Encodes a Nuclear Zinc Finger Protein That Binds DNA and Functions as a Transcriptional Repressor", *Mol. Cell. Biol.* 16: 4024-4034 (1996).
Dreier, et al., "Insights into the Molecular Recogntion of the 5'-GNN-3' Family of Sequences by Zinc Finger Domains", *J. Mol. Biol.* 303: 489-502 (2000).
Celenza, et al., "A Yeast Gene That is Essential for Release from Glucose Repression Encodes a Protein Kinase", *Science 233*: 1175-1180 (1986).
Singh, et al., "Molecular Cloning of an Enhancer Binding Protein: Isolation by Screening of an Expression Library with a Recognition Site DNA", *Cell 52*: 415-423 (1988).
Kinzler, et al., "The *GLI* Gene is a Member of the *Kruppel* Family of Zinc Finger Proteins", *Nature 332*: 371-374 (1988).
Debs, et al., "Regulation Gene Expression in Vivo by Liposome-Mediated Delivery of a Purified Transcription Factor", *J. Biol. Chem.* 265: 10189-10192 (1990).
Kudla, et al. "The Regulatory Gene areA Mediating Nitrogen Metabolite Repression in *Aspergillus nidulans*. Mutations Affecting Specificity of Gene Activation Alter a Loop Residue of a Putative Zinc Finger", *EMBO J.* 9: 1355-1364 (1990).
Wright, et al., "Expression of a Zinc Finger Gene in HTLV-I-and HTLV-II-Transformed Cells", *Science 248*: 588-591 (1990).
Bergqvist, et al., "Loss of DNA-Binding and New Transcriptional *trans*-activationFunction in Polyomavirus Large T-antigen with Mutation of Zinc Finger Motif", *Nucleic Acids Res.* 18: 2715-2720 (1990).
South, et al., "The Nucleocapsid Protein Isolated from HIV-1 Particles Binds Zinc and Forms Retroviral-Type Zinc Fingers", *Biochemistry 29*: 7786-7789 (1990).

(Continued)

Primary Examiner—Terry McKelvey
(74) *Attorney, Agent, or Firm*—Catalyst Law Group, APC; Michael B. Farber, Esq.

(57) ABSTRACT

Polypeptides that contain from 2 to 12 zinc finger-nucleotide binding regions that bind to nucleotide sequences of the formula (ANN)2–12 are provided. Polynucleotides that encode such polypeptides and methods of regulating gene expression with such polypeptides and polynucleotides are also provided.

6 Claims, 9 Drawing Sheets

OTHER PUBLICATIONS

Rauscher, III, et al., "Binding of the Wilms' Tumor Locus Zinc Finger Protein to the EGR-1 Consensus Sequence", *Science 250*: 1259-1262 (1990).

Nardelli, et al., "Base Sequence Discrimination by Zinc-Finger DNA-Binding Domains", *Nature 349*: 175-178 (1991).

Theisen, et al., "Amino Acid Substitutions in the SP1 Zinc Finger Domain Alter the DNA Binding Affinity to Cognate SP1 Target Site", *Biochem. Biophys. Res. Commun. 175*: 333-338 (1991).

Pavletich, et al., "Zinc Finger-DNA Recognition: Crystal Structure of a Zif268-DNA Complex at 2.1 Å", *Science 252*: 809-817 (1991).

DiBello, et al., "The Drosophila *Broad-Complex* Encodes a Family of Related Proteins Containing Zinc Fingers", *Genetics 129*: 385-397 (1991).

Ray, et al., "Repressor to Activator Switch by Mutations in the First Zn Finger of the Glucocorticoid Receptor: Is Direct DNA Binding Necessary", *Proc. Natl. Acad. Sci. USA 88*: 7086-7090 (1991).

Agarwal, et al., "Stimulation of Transcript Elongation Requires both the Zinc Finger and RNA Polymerase II Binding Domains of Human TFIIS", *Biochemistry 30*: 7842-7851 (1991).

Antao, et al., "A Thermodynamic Study of Unusually Stable RNA and DNA Hairpins", *Nucleic Acids Res. 19*: 5901-5905 (1991).

Webster, et al., "Conversion of the EIA $Cys_4$ Zinc Finger to a Nonfunctional $His_2Cys_2$ Zinc Finger by a Single Point Mutation", *Proc. Natl. Acad. Sci, USA 88*: 9989-9993 (1991).

Wilson, et al., "In Vivo Mutational Analysis of the NGFI-A Zinc Fingers:", *J. Biol. Chem. 267*: 3718-3724 (1992).

Thukral, et al., "Mutations in the Zinc Fingers of ADRI that Change the Specificity of DNA Binding and Transactivation", *Mol. Cell. Biol. 12*: 2784-2792 (1992).

Quigley, et al., "Complete Androgen Insensitivity Due to Deletion of Exon C of the Androgen Receptor Gene Highlights the Functional Importance of the Second Zinc Finger of the Androgen in Vivo", *Mol. Endocrinol. 6*: 1103-1112 (1992).

Barbas III, et al., "Semisynthetic Combinatorial Antibody Libraries: A Chemical Solution to the Diversity Problem", *Proc. Natl. Acad. Sci. USA 89*: 4457-4461 (1992).

Hirst, et al., "Discrimination of DNA Response Elements for Thyroid Hormone and Estrogen is Dependent on Dimerization of Receptor DNA Binding Domains", *Proc. Natl. Acad. Sci. USA 89*: 5527-5531 (1992).

Desjarlais, et al., "Redesigning the DNA-Binding Specificity of a Zinc Finger Protein: A Data Base-Guided Approach", *PROTEINS: Structure, Function, and Genetics 12*: 101-104 (1992).

Nardelli, et al., "Zinc Finger-DNA Recognition: Analysis of Base Specificity by Site-Directed Mutagenesis", *Nucleic Acids Res. 20*: 4137-4144 (1992).

Crozatier, et al., "Single Amino Acid Exchanges in Separate Domains of the Drosophila Serendipity δ Zinc Finger Protein Cause Embryonic and Sex Biased Lethality", *Genetics 131*: 905-916 (1992).

Qian, et al., "Two-Dimensional NMR Studies of the Zinc Finger Motif: Solution Structures and Dynamics of Mutant ZFY Domains Containing Aromatic Substitutions in the Hydrophobic Core", *Biochemistry 31*: 7463-7476 (1992).

Desjarlais, et al., "Toward Rules Relating Zinc Finger Protein Sequences and DNA Binding Site Preferences", *Natl. Acad. Sci. USA 39*: 7345-7349 (1992).

Hayes, et al., "Locations of Contacts between Individual Zinc Fingers of *Xenopus laevis* Transcription Factor IIIA and the Internal Control Region of a 5S RNA Gene", *Biochemistry 31*: 11600-11605 (1992).

Jacobs, "Determination of the Base Recognition Positions of Zinc Fingers from Sequence Analysis", *EMBO J. 11*: 4507-4517 (1992).

Pabo, et al., "Transcription Factors: Structural Families and Principles of DNA Recognition", *Annu. Rev. Biochem. 61*: 1053-1095 (1992).

Saleh, et al., "A Novel Zinc Finger Gene on Human Chromosome 1 qter that is Alternatively Spliced in Human Tissues and Cell Lines", *Am. J. Hum. Genet. 52*:192-203 (1993).

Hoffman, et al., "Structures of DNA-Binding Mutant Zinc Finger Domains: Implications for DNA Binding", *Protein Sci. 2*: 951-965 (1993).

Bellefroid, et al., "Clustered Organization of Homologous KRAB Zinc-Finger Genes with enhanced Expression in Human T. Lymphoid Cells", *EMBO J. 12*: 1363-1374 (1993).

Yu, et al., "A Hairpin Ribozyme Inhibits Expression of Diverse Strains of Human Immunodeficiency Virus Type 1", *Proc. Natl. Acad. Sci. USA 90*: 6340-6344 (1993).

Rollins, et al., "Role of TFIIIA Zinc Fingers in Vivo: Analysis of Single-Finger Function in Developing *Xenopus* Embryos", *Mol. Cell. Biol. 13*: 4776-4783 (1993).

Julian, et al., "Replacement of $His^{23}$ by Cys in a Zinc Finger of HIV-1 $NC_p7$ Led to a Change in $^1H$ NMR-Derived 3D Structure and to a Loss of Biological Activity", *FEBS 331*: 43-48 (1993).

Pavletich, et al., "Crystal Structure of a Five-Finger GLI-DNA Complex: New Perspectives on Zinc Fingers", *Science 261*: 1701-1707 (1993).

Fairall, et al., "The Crystal Structure of a Two Zinc-Finger Peptide Reveals an Extension to the Rules for Zinc-Finger/DNA Recognition", *Nature 366*: 483-487 (1993).

Rebar, et al., "Zinc Finger Phage: Affinity Selection of Fingers with New DNA-Binding Specificities", *Science 263*: 671-673 (1994).

Jamieson, et al., "In Vitro Selection of Zinc Fingers with Altered DNA-Binding Specificity", *Biochemistry 33*: 5689-5695 (1994).

Choo, et al., "Toward a Code for the Interactions of Zinc Fingers with DNA: Selection of Randomized Fingers Displayed on Phage", *Proc. Natl. Acad. Sci. USA 91*: 11163-11167 (1994).

Wu, et al., "Building Zinc Fingers by Selection: Toward a Therapeutic Application", *Proc. Natl. Acad. Sci. USA 92*: 344-348 (1995).

Taylor, et al., "Designing Zinc-Finger ADRI Mutants with Altered Specificity of DNA Binding to T in UAS1 Sequences", *Biochemistry 34*: 3222-3230 (1995).

Elrod-Erickson, et al., "Zif268 Protein-DNA Complex Refined at 1.6 Å: A Model System for Understanding Zinc Finger-DNA Interactions", *Structure 4*: 1171-1180 (1996).

Jamieson, et al., "A Zinc Finger Directory for High-Affinity DNA Recognition", *Proc. Natl. Acad. Sci. USA 93*: 12834-12839 (1996).

Houbavity, et al., "Cocrystal Structure of YY1 Bound to the Adeno-Associated Virus P5 Initiator", *Proc. Natl. Acad. Sci. USA 93*: 13577-13582 (1996).

Kim, et al., "A 2.2 Å Resolution Crystal Structure of a Designed Zinc Finger Protein Bound to DNA", *Nature Structural Biology 3*: 940-945 (1996).

Greisman, et al., "A General Strategy for Selecting High-Affinity Zinc Finger Proteins for Diverse DNA Target Sites", *Science 275*: 657-661 (1997).

Narayan, et al., "Structures of Zinc Finger Domains from Transcription Factor Sp1", *J. Biol. Chem. 272*: 7801-7809 (1997).

Liu, et al., "Design of Polydactyl Zinc-Finger Proteins for Unique Addressing within Complex Genomes", *Proc. Natl. Acad. Sci. USA 94*: 5525-5530 (1997).

Isalan, et al., "Synergy Between Adjacent Zinc Fingers in Sequence-Specific DNA Recognition", *Proc. Natl. Acad. Sci. USA 94*: 5617-5621 (1997).

Wuttke, et al., "Solution Structure of the First Three Zinc Fingers of TFIIIA Bound to the Cognate DNA Sequence: Determinants of Affinity and Sequence Specificity", *J. Mol. Biol. 273*: 183-206 (1997).

Elrod-Erickson, et al., "High Resolution Structures of Variant Zif268-DNA Complexes: Implications for Understanding Zinc Finger-DNA Recognition", *Structure 6*: 451-464 (1998).

Nolte, et al., "Differing Roles for Zinc Fingers in DNA Recognition: Structures of a Six-Finger Transcription Factor IIIA Complex", *Proc. Natl. Acad. Sci. USA 95*: 2938-2943 (1998).

Isalan, et al., "Comprehensive DNA Recognition through Concerted Interactions from Adjacent Zinc Fingers", *Biochemistry 37*: 12026-12033 (1998).

Gebelein, et al., "A Novel Profile of Expressed Sequences Tags for Zinc Finger Encoding Genes from the Poorly Differentiated Exocrine Pancreatic Cell Line AR41P", *Cancer Lett. 105*: 225-231 (1996).

Ogawa, et al., "Enhanced Expression in Seminoma of Human Zinc Finger Genes Located on Chromosome 19", *Cancer Genet. Cytogenet. 100*: 36-42 (1998).

Miller, et al., "Repetitive Zinc-Binding Domains in the Protein Transcription Factor IIIA from Xenopus Oocytes", *EMBO J. 4*: 1609-1614 (1985).

Sadowski, et al., "GAL4-VP16 is an Unusually Potent Transcriptional Activator", *Nature 335*: 563-564 (1988).

Lee, et al., "Three-Dimensional Solution Structure of a Single Zinc Finger DNA-Binding Domain", *Science 245*: 635-637 (1989).

Barbas, et al., "Assembly of Combinatorial Antibody Libraries on Phage Surfaces: The Gene III Site", *Proc. Natl. Acad. Sci. USA 88*: 7978-7982 (1991).

Kim, et al., "Design of TATA Box-Binding Protein/Zinc Finger Fusions for Targeted Regulation of Gene Expression", *Proc. Natl. Acad. Sci. USA 94*: 3616-3620 (1997).

Rader, et al., "Phage Display of Combinatorial Antibody Libraries", *Curr. Opin. Biotechnology 8*: 503-508 (1997).

Kim, et al., "Transcriptional Repression by Zinc Finger Peptides", *J. Biol. Chem. 272*: 29795-29800 (1997).

Becrli, et al., "Toward Controlling Gene Expression at Will: Specific Regulation of the *erbB-2/HER-2* Promoter by Using Polydactyl Zinc Finger Proteins Constructed from Modular Building Blocks", *Proc. Natl. Acad. Sci. USA 95*: 14628-14633 (1998).

Segal, et al., "Toward Controlling Gene Expression at Will: Selection and Design of Zinc Finger Domains Recognizing Each of the 5'-GNN-3' DNA Target Sequences", *Proc. Natl. Acad. Sci. USA 96*: 2758-2763 (1999).

* cited by examiner

Number in parenthesis = SEQ ID NO

AAA

| | -2 | -1 | 1 | 2 | 3 | 4 | 5 | 6 | |
|---|---|---|---|---|---|---|---|---|---|
| 1 | S | T | N | T | K | L | H | A | (7) |
| 1 | S | S | D | R | T | L | R | R | (8) |
| 2 | S | T | K | E | R | L | K | T | (9) |
| 1 | S | Q | R | A | N | L | R | A | (10) |

ACA

| | -2 | -1 | 1 | 2 | 3 | 4 | 5 | 6 | |
|---|---|---|---|---|---|---|---|---|---|
| 2 | S | P | A | D | L | T | R |   | (11) |
| 2* | S | S | H | S | D | L | V | R | (12) |
| 1* | S | N | G | G | E | L | I | R | (13) |
| 1 | S | H | Q | L | I | L | L | K | (14) |
| 1 | S | S | R | M | D | L | K | R | (15) |

AGA

| | -2 | -1 | 1 | 2 | 3 | 4 | 5 | 6 | |
|---|---|---|---|---|---|---|---|---|---|
| 4* | S | R | S | D | H | L | T | N | (16) |
| 1 | S | Q | L | A | H | L | R | A | (17) |

ATA

| | -2 | -1 | 1 | 2 | 3 | 4 | 5 | 6 | |
|---|---|---|---|---|---|---|---|---|---|
| 3* | S | Q | A | S | S | L | K | A | (18) |
| 1 | S | Q | K | S | S | L | I | A | (19) |

AAC

| | -2 | -1 | 1 | 2 | 3 | 4 | 5 | 6 | |
|---|---|---|---|---|---|---|---|---|---|
| 2* | S | R | K | D | N | L | K | N | (20) |
| 1 | S | D | S | G | N | L | R | V | (21) |
| 1 | S | D | R | R | N | L | R | R | (22) |

ACC

| | -2 | -1 | 1 | 2 | 3 | 4 | 5 | 6 | |
|---|---|---|---|---|---|---|---|---|---|
| 4 | S | D | K | K | D | L | T | R | (23) |

AGC

| | -2 | -1 | 1 | 2 | 3 | 4 | 5 | 6 | |
|---|---|---|---|---|---|---|---|---|---|
| 1* | S | D | A | S | H | L | H | T | (24) |
| 1 | S | T | N | T | G | L | K | N | (25) |
| 1 | S | T | R | M | S | L | S | T | (26) |
| 1 | S | N | H | D | A | L | R | A | (27) |

ATC

| | -2 | -1 | 1 | 2 | 3 | 4 | 5 | 6 | |
|---|---|---|---|---|---|---|---|---|---|
| 2* | S | R | R | S | A | C | R | R | (28) |
| 2* | S | R | R | S | S | C | R | K | (29) |

AAG

| | -2 | -1 | 1 | 2 | 3 | 4 | 5 | 6 | |
|---|---|---|---|---|---|---|---|---|---|
| 3 | S | R | S | D | T | L | S | N | (30) |
| 3 | S | R | M | G | N | L | I | R | (31) |

ACG

| | -2 | -1 | 1 | 2 | 3 | 4 | 5 | 6 | |
|---|---|---|---|---|---|---|---|---|---|
| 3 | S | R | T | D | T | L | R | D | (32) |
| 3* | S | R | A | H | D | L | V | R | (33) |

AGG

| | -2 | -1 | 1 | 2 | 3 | 4 | 5 | 6 | |
|---|---|---|---|---|---|---|---|---|---|
| 3 | S | R | S | D | H | L | A | E | (34) |

ATG

| | -2 | -1 | 1 | 2 | 3 | 4 | 5 | 6 | |
|---|---|---|---|---|---|---|---|---|---|
| 4 | S | R | R | D | A | L | N | V | (35) |

AAT

| | -2 | -1 | 1 | 2 | 3 | 4 | 5 | 6 | |
|---|---|---|---|---|---|---|---|---|---|
| 1 | S | T | T | G | N | L | T | V | (36) |
| 1* | S | T | S | G | N | L | L | V | (37) |
| 1 | S | T | L | T | I | L | K | N | (38) |
| 1 | S | R | M | S | T | L | R | H | (39) |

ACT

| | -2 | -1 | 1 | 2 | 3 | 4 | 5 | 6 | |
|---|---|---|---|---|---|---|---|---|---|
| 2 | S | T | R | T | D | L | L | R | (40) |
| 1* | S | T | K | T | D | L | K | R | (41) |
| 1 | S | T | H | I | D | L | I | R | (42) |

AGT

| | -2 | -1 | 1 | 2 | 3 | 4 | 5 | 6 | |
|---|---|---|---|---|---|---|---|---|---|
| 4 | S | H | R | T | T | L | L | N | (43) |

ATT

| | -2 | -1 | 1 | 2 | 3 | 4 | 5 | 6 | |
|---|---|---|---|---|---|---|---|---|---|
| 3* | S | T | S | H | G | L | T | T | (44) |
| 1 | S | H | K | N | A | L | Q | N | (45) |

FIG. 2

Number in parenthesis = SEQ ID NO

Number in parenthesis = SEQ ID NO

Number in parenthesis = SEQ ID NO

Number in parenthesis = SEQ ID NO

| P | F 1 | F 2 | F 3 | F 4 | F 5 | F 6 |
|---|---|---|---|---|---|---|
| Aart | RRD-A-LNV (58) 3'-GTA-5' | RED-N-LHT (71) 3'-GAT-5' | QLA-H-LRA (54) 3'-AGA-5' | QRA-N-LRA (46) 3'-AAA-5' | DKK-D-LTR (51) 3'-CCA-5' | RSD-H-LAE (55) 3'-GGA-5' |
| E2X | DKK-D-LTR (51) 3'-CCA-5' | QSS-H-LVR (107) 3'-AGG-5' | QSS-N-LVR (108) 3'-AAG-5' | DKK-D-LTR (51) 3'-CCA-5' | RSD-H-LTN (63) 3'-GGA-5' | QSS-H-LVR (107) 3'-AGG-5' |
| E3Y | DPG-A-LRV (109) 3'-CTA-5' | RSD-N-LVR (110) 3'-GAG-5' | QSG-D-LRR (111) 3'-ACG-5' | QLA-H-LRA (54) 3'-AGA-5' | DCR-D-LAR (112) 3'-CCG-5' | DKK-D-LTR (51) 3'-CCA-5' |
| E3Z | DCR-D-LAR (112) 3'-CCG-5' | QSG-D-LRR (111) 3'-ACG-5' | QSG-D-LRR (111) 3'-ACG-5' | DCR-D-LAR (112) 3'-CCG-5' | DKK-D-LTR (51) 3'-CCA-5' | TTG-N-LTV (49) 3'-TAA-5' |

FIG. 4A

ZINC FINGER BINDING DOMAINS FOR NUCLEOTIDE SEQUENCE ANN

This invention was made with government support under Contract No. GM 53910 by the National Institutes of Health. The government has certain rights in the invention.

TECHNICAL FIELD OF THE INVENTION

The field of this invention is zinc finger protein binding to target nucleotides. More particularly, the present invention pertains to amino acid residue sequences within the α-helical domain of zinc fingers that specifically bind to target nucleotides of the formula 5'-(ANN)-3'.

BACKGROUND OF THE INVENTION

The construction of artificial transcription factors has been of great interest in the past years. Gene expression can be specifically regulated by polydactyl zinc finger proteins fused to regulatory domains.

Zinc finger domains of the $Cys_2$-$His_2$ family have been most promising for the construction of artificial transcription factors due to their modular structure. Each domain consists of approximately 30 amino acids and folds into a ββα structure stabilized by hydrophobic interactions and chelation of a zinc ion by the conserved $Cys_2$-$His_2$ residues. To date, the best characterized protein of this family of zinc finger proteins is the mouse transcription factor Zif 268 [Pavletich et al., (1991) Science 252(5007), 809–817; Elrod-Erickson et al., (1996) Structure 4(10), 1171–1180]. The analysis of the Zif 268/DNA complex suggested that DNA binding is predominantly achieved by the interaction of amino acid residues of the α-helix in position-1, 3, and 6 with the 3', middle, and 5' nucleotide of a 3 bp DNA subsite, respectively. Positions 1, 2 and 5 have been shown to make direct or water-mediated contacts with the phosphate backbone of the DNA. Leucine is usually found in position 4 and packs into the hydrophobic core of the domain. Position 2 of the α-helix has been shown to interact with other helix residues and, in addition, can make contact to a nucleotide outside the 3 bp subsite [Pavletich et al., (1991) Science 252(5007), 809–817; Elrod-Erickson et al., (1996) Structure 4(10), 1171–1180; Isalan, M. et al., (1997) Proc Natl Acad Sci USA 94(11), 5617–5621].

The selection of modular zinc finger domains recognizing each of the 5'-GNN-3' DNA subsites with high specificity and affinity and their refinement by site-directed mutagenesis has been demonstrated. These modular domains can be assembled into zinc finger proteins recognizing extended 18 bp DNA sequences which are unique within the human or any other genome. In addition, these proteins function as transcription factors and are capable of altering gene expression when fused to regulatory domains and can even be made hormone-dependent by fusion to ligand-binding domains of nuclear hormone receptors. To allow the rapid construction of zinc finger-based transcription factors binding to any DNA sequence it is important to extend the existing set of modular zinc finger domains to recognize each of the 64 possible DNA triplets. This aim can be achieved by phage display selection and/or rational design.

Due to the limited structural data on zinc finger/DNA interaction rational design of zinc proteins is very time consuming and may not be possible in many instances. In addition, most naturally occurring zinc finger proteins consist of domains recognizing the 5'-GNN-3' type of DNA sequences. Only a few zinc finger domains binding to sequences of the 5'-ANN-3' type are found in naturally occurring proteins, like finger 5 (5'-AAA-3') of Gfi-1 [Zweidler-McKay et al., (1996) Mol. Cell. Biol. 16(8), 4024–4034], finger 3 (5'-AAT-3') of YY1 [Hyde-DeRuyscher, et al., (1995) Nucleic Acids Res. 23(21), 4457–4465], fingers 4 and 6 (5'-[A/G]TA-3') of CF2II [Gogos et al., (1996) PNAS 93, 2159–2164]and finger 2 (5'-AAG-3') of TTK [Fairall et al., (1993) Nature (London) 366(6454), 483–7]. However, in structural analysis of protein/DNA complexes by X-ray or NMR studies, interaction of the amino acid residue in position 6 of the a-helix with a nucleotide other than 5' guanine was never observed. Therefore, the most promising approach to identify novel zinc finger domains binding to DNA target sequences of the type 5'-ANN-3',5'-CNN-3' or 5'-TNN-3' is selection via phage display. The limiting step for this approach is the construction of libraries that allow the specification of a 5' adenine, cytosine or thymine. Phage display selections have been based on Zif268 in which in which different fingers of this protein where randomized [Choo et al., (1994) Proc. Natl. Acad. Sci. U.S.A. 91(23), 11168–72; Rebar et al., (1994) Science (Washington, D.C., 1883-) 263(5147), 671–3; Jamieson et al., (1994) Biochemistry 33, 5689–5695; Wu et al., (1995) PNAS 92, 344–348; Jamieson et al., (1996) Proc Natl Acad Sci USA 93, 12834–12839; Greisman et al., (1997) Science 275(5300), 657–661]. A set of 16 domains recognizing the 5'-GNN-3' type of DNA sequences has previously been reported from a library where finger 2 of C7, a derivative of Zif268 [U.S. Pat. No. 6,140,081, the disclosure of which is incorporated herein by reference; Wu et al., (1995) PNAS 92, 344–348 Wu, 1995 #164], was randomized [Segal et al., (1999) Proc Natl Acad Sci USA 96(6), 2758–2763]. In such a strategy, selection is limited to domains recognizing 5'-GNN-3' or 5'-TNN-3' due to the $Asp^2$ of finger 3 making contact with the complementary base of a 5' guanine or thymine in the finger-2 subsite [Pavletich et al., (1991) Science 252(5007), 809–817; Elrod-Erickson et al., (1996) Structure 4(10), 1171–1180]. The limited modularity of zinc finger domains, which may in some cases recognize a nucleotide outside the 3 bp subsite, has been discussed intensively [Wolfe et al., (1999) Annu. Rev. Biophys. Biomol. Struct. 3, 183–212; Segal et al., (2000) Curr Opin Chem Biol 4(1), 34–39; Pabo et al., (2000) J. Mol. Biol. 301, 597–624; Choo et al., (2000) Curr. Opin. Struct. Biol. 10, 411–416]. One approach to overcome the limitations imposed by target site overlap is the randomization of amino acid residues in two adjacent fingers [Jamieson et al., (1996) Proc Natl Acad Sci USA 93, 12834–12839; Isalan et al., (1998) Biochemistry 37(35), 12026–12033]. A second, but time consuming approach is the sequential selection of fingers 1 to 3 for a specific 9 bp target site which accounts for the individual structure and mode of DNA binding of each finger and its surrounding fingers [Greisman et al., (1997) Science 275(5300), 657–661; Wolfe et al., (1999) J Mol Biol 285(5), 1917–1934].

The present approach is based on the modularity of zinc finger domains that allows the rapid construction of zinc finger proteins by the scientific community and demonstrates that the concerns regarding limitation imposed by cross-subsite interactions only occurs in a limited number of cases. The present disclosure introduces a new strategy for selection of zinc finger domains specifically recognizing the 5'-ANN-3' type of DNA sequences. Specific DNA-binding properties of these domains was evaluated by a multi-target ELISA against all sixteen 5'-ANN-3' triplets. These domains can be readily incorporated into polydactyl proteins containing various numbers of 5'-ANN-3' domains, each specifically recognizing extended 18 bp sequences. Furthermore, these domains were able to specifically alter gene expression when fused to regulatory domains. These results underline the feasibility of constructing polydactyl proteins from pre-defined building blocks. In addition, the domains characterized here greatly increase the number of DNA sequences that can be targeted with artificial transcription factors.

BRIEF SUMMARY OF THE INVENTION

The present disclosure teaches the construction of a novel phage display library enabling the selection of zinc finger domains recognizing the 5'-ANN-3' type of DNA sequences. Such domains were isolated and showed exquisite binding specificity for the 3 bp target site for against which they were selected. These zinc finger domains were engrafted into 6-finger proteins which bound specifically to their 18 bp target site with affinities in the pM to lower nM range. When fused to regulatory domains, one artificial 6-finger protein containing five 5'-ANN-3' and one 5'-TNN-3' domain regulated a luciferase reporter gene under control of a minimal promoter containing the zinc finger-binding site and a TATA-box. In addition, 6-finger proteins assembled from 5'-ANN-3' and 5'-GNN-3' domains showed specific transcriptional regulation of the endogenous erbB-2 and erbB-3 genes, respectively. These results show that modular zinc finger domains can be selected binding to 3 bp target sites other than 5'-GNN-3' and that they are suitable as additional modules to create artificial transcription factors, thereby greatly increasing the number of sequences that can be targeted by DNA-binding proteins built from pre-defined zinc finger domains.

In one embodiment, a polypeptide of the invention contains a binding region that has an amino acid residue sequence with the same nucleotide binding characteristics as any of SEQ ID NOs:SEQ ID NO: 7–71 and 107–112. Such a polypeptide competes for binding to a nucleotide target with any of SEQ ID NOs:SEQ ID NO: 7–71 and 107–112. Preferably, the binding region has the amino acid residue sequence of any of SEQ ID NOs:SEQ ID NO: 7–71 and 107–112. Preferably, the binding region has the amino acid residue sequence of any of SEQ ID NOs: 46–70. More preferably, the binding region has the amino acid residue sequence of any of SEQ ID NOs: 10, 11, 17, 19, 21, 23–30, 32, 34–36, 42, 43 or 45.

In another aspect, the present invention provides a composition that contains from about 2 to about 12 of a zinc finger nucleotide binding polypeptide as disclosed herein. Such a composition binds to a nucleotide sequence that contains a sequence of the formula 5'-(CNN)$_n$-3', where N is A, C, G or T and n is 2 to 12. Preferably, the composition contains from about 2 to about 6 zinc finger nucleotide binding polypeptides binds to a nucleotide sequence that comprises a sequence of the formula 5'-(CNN)$_n$-3', where n is 2 to 6.

Thus, the present invention provides an isolated and purified polypeptide that contains from 2 to 12 zinc finger-nucleotide binding peptides, at least one of which peptides contains a nucleotide binding region having the sequence of any of SEQ ID NO: 7–71 and 107–112. In a preferred embodiment, the polypeptide contains from 2 to 6 zinc finger-nucleotide binding peptides. Such a polypeptide binds to a nucleotide that contains the sequence 5'-(ANN)$_n$-3', wherein each N is A, C, G, or T and where n is 2 to 12. Preferably, each of the peptides binds to a different target nucleotide sequence. A polypeptide of this invention can be operatively linked to one or more transcription regulating factors such as a repressor or an activator.

Polynucleotides that encode the polypeptides, expression vectors containing the polynucleotides and cells transformed with expression vectors are also provided.

In a related aspect, the present invention provides a process of regulating expression of a nucleotide sequence that contains the sequence (5'-ANN)$_n$-3', where n is an integer from 2 to 12. The process includes the step of exposing the nucleotide sequence to an effective amount of a polypeptide of this invention under conditions in which the polypeptide binds to expression regulating sequences of the nucleotide. Thus, the sequence 5'-(ANN)$_n$-3' can be located in the transcribed region of the nucleotide sequence, a promotor region of the nucleotide sequence or within an expressed sequence tag. A polypeptide is preferably operatively linked to one or more transcription regulating factors.

BRIEF DESCRIPTION OF THE DRAWINGS

FIG. 2 shows amino acid sequences of finger-2 recognition helices from selected clones. For each DNA target site several single clones were sequenced after the sixth round of panning and the amino acid determined to evaluate the selection. The DNA recognition subsite of finger 2 is shown on the left of each set, followed by the number of each occurrence. The position of the amino acid residue within the α-helix is shown at the top. Boxed sequences were studied in detail and represent the best binders of each set. Sequences marked with an asterisk were additional analyzed clones. [1]Clones with a Ser[4] to Cys[4] mutation in finger 3. [2]Sequences determined after subcloning the zinc finger sequences from the DNA pool after the sixth round of selection into a modified pMAL-c2 vector.

DETAILED DESCRIPTION OF THE INVENTION

I. Zinc Finger Polypeptides

Figure 1:
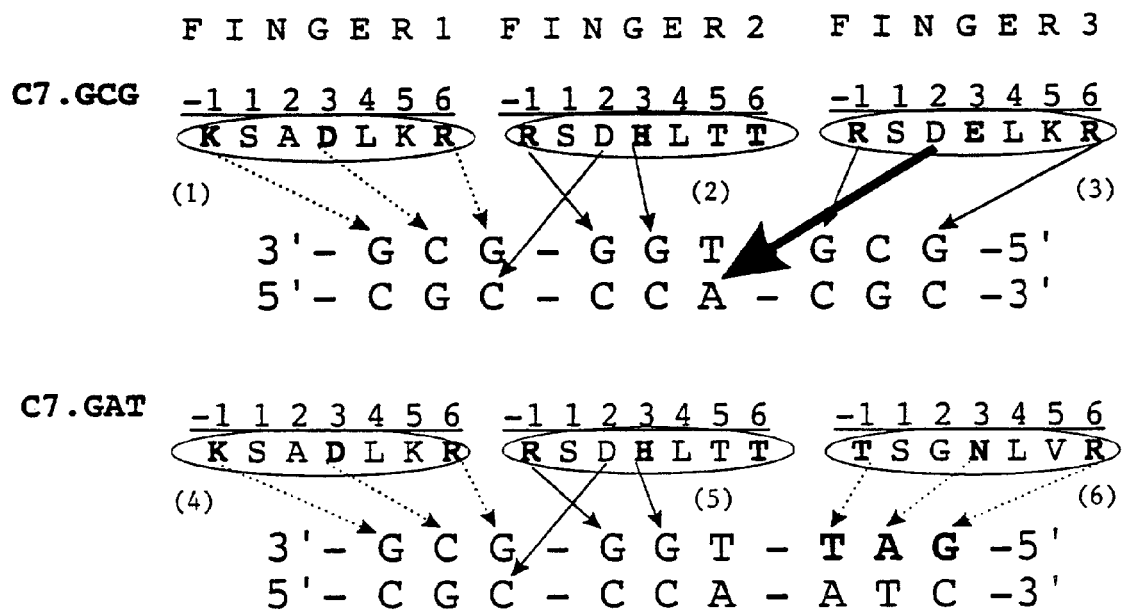
FIG. 1, in two panels designated 1A and 1B, shows, schematically, construction of the zinc finger phage display library (A) and multitarget specificity ELISA for the C7 proteins (B). In 1A, solid arrows show interactions of the amino acid residues of the zinc finger helices with the nucleotides of their binding site as determined by x-ray crystallography of Zif268 and dotted lines show proposed interactions. B, upper panel:; black bars: target sites of the type 5'-GNN-3' in finger-2 position; gray bar: 5'-TGG-3'; white bars: evaluation of the 5' recognition of finger 2 against a mixture of all 16 5'-XNN-3' subsites where X represents 5'-adenine, 5'-cytosine, 5'-guanine, or 5'-thymine, respectively. B, lower panel: Multitarget specificity ELISA for the C7.GAT protein; black bars: target sites of the type 5'-TNN-3' in finger-2 position; white bars: evaluation of the 5' recognition of finger 2 against a mixture of all 16 5'-XNN-3' subsites. Affinities of the proteins to their DNA target site are given in the right upper corner of each graph.

The present invention provides isolated and purified polypeptides that contain from 2 to 12 nucleotide binding domain peptides derived from zinc finger proteins. The nucleotide binding domain peptides are derived from the α-helical portion of the zinc finger proteins. Preferred such nucleotide binding domain peptides have the amino acid residue sequence of any of SEQ ID NOs: 7–71 or 107–112. Preferably, the peptide has the amino acid residue sequence of any of SEQ ID NOs: 46–70. More preferably, the peptide has the amino acid residue sequence of any of SEQ ID NOs: 10, 11, 17, 19, 21, 23–30, 32, 34–36, 42, 43 or 45. Each of the peptides is designed and made to specifically bind nucleotide target sequences corresponding to the formula 5'-ANN-3', where N is any nucleotide (i.e., A, C, G or T).

Thus, a polypeptide of this invention binds to a nucleotide sequence 5'-(ANN)$_n$-3', where n is an integer from 2 to 12. Preferably, n is from 2 to 6.

A compound of this invention is an isolated zinc finger-nucleotide binding polypeptide that binds to a ANN nucleotide sequence and modulates the function of that nucleotide sequence. The polypeptide can enhance or suppress transcription of a gene, and can bind to DNA or RNA. A zinc finger-nucleotide binding polypeptide refers to a polypeptide which is a mutagenized form of a zinc finger protein or one produced through recombination. A polypeptide may be a hybrid which contains zinc finger domain(s) from one protein linked to zinc finger domain(s) of a second protein, for example. The domains may be wild type or mutagenized. A polypeptide includes a truncated form of a wild type zinc finger protein. Examples of zinc finger proteins from which a polypeptide can be produced include TFIIIA and zif268.

A zinc finger-nucleotide binding polypeptide of this invention comprises a unique heptamer (contiguous sequence of 7 amino acid residues) within the α-helical domain of the polypeptide, which heptameric sequence determines binding specificity to a target nucleotide. That heptameric sequence can be located anywhere within the α-helical domain but it is preferred that the heptamer extend from position-1 to position 6 as the residues are conventionally numbered in the art. A polypeptide of this invention can include any β-sheet and framework sequences known in the art to function as part of a zinc finger protein. A large number of zinc finger-nucleotide binding polypeptides were made and tested for binding specificity against target nucleotides containing a ANN triplet.

The zinc finger-nucleotide binding polypeptide derivative can be derived or produced from a wild type zinc finger protein by truncation or expansion, or as a variant of the wild type-derived polypeptide by a process of site directed mutagenesis, or by a combination of the procedures. The term "truncated" refers to a zinc finger-nucleotide binding polypeptide that contains less that the full number of zinc fingers found in the native zinc finger binding protein or that has been deleted of non-desired sequences. For example, truncation of the zinc finger-nucleotide binding protein TFIIIA, which naturally contains nine zinc fingers, might be a polypeptide with only zinc fingers one through three. Expansion refers to a zinc finger polypeptide to which additional zinc finger modules have been added. For example, TFIIIA may be extended to 12 fingers by adding 3 zinc finger domains. In addition, a truncated zinc finger-nucleotide binding polypeptide may include zinc finger modules from more than one wild type polypeptide, thus resulting in a "hybrid" zinc finger-nucleotide binding polypeptide.

The term "mutagenized" refers to a zinc finger derived-nucleotide binding polypeptide that has been obtained by performing any of the known methods for accomplishing random or site-directed mutagenesis of the DNA encoding the protein. For instance, in TFIIIA, mutagenesis can be performed to replace nonconserved residues in one or more of the repeats of the consensus sequence. Truncated zinc finger-nucleotide binding proteins can also be mutagenized.

Examples of known zinc finger-nucleotide binding polypeptides that can be truncated, expanded, and/or mutagenized according to the present invention in order to inhibit the function of a nucleotide sequence containing a zinc finger-nucleotide binding motif includes TFIIIA and zif268. Other zinc finger-nucleotide binding proteins will be known to those of skill in the art.

A polypeptide of this invention can be made using a variety of standard techniques well known in the art. Phage display libraries of zinc finger proteins were created and selected under conditions that favored enrichment of sequence specific proteins. Zinc finger domains recognizing a number of sequences required refinement by site-directed mutagenesis that was guided by both phage selection data and structural information. Previously we reported the characterization of 16 zinc finger domains specifically recognizing each of the 5'-GNN-3' type of DNA sequences, that were isolated by phage display selections based on C7, a variant of the mouse transcription factor Zif268 and refined by site-directed mutagenesis [Segal et al., (1999) *Proc Natl Acad Sci USA* 96(6), 2758–2763; Dreier et al., (2000) *J. Mol. Biol.* 303, 489–502]. The molecular interaction of Zif268 with its target DNA 5'-GCG TGG GCG-3' (SEQ ID NO: 76) has been characterized in great detail. In general, the specific DNA recognition of zinc finger domains of the $Cys_2$-$His_2$ type is mediated by the amino acid residues-1, 3, and 6 of each α-helix, although not in every case are all three residues contacting a DNA base. One dominant cross-subsite interaction has been observed from position 2 of the recognition helix. $Asp^2$ has been shown to stabilize the binding of zinc finger domains by directly contacting the complementary adenine or cytosine of the 5' thymine or guanine, respectively, of the following 3 bp subsite. These non-modular interactions have been described as target site overlap. In addition, other interactions of amino acids with nucleotides outside the 3 bp subsites creating extended binding sites have been reported [Pavletich et al., (1991) *Science* 252(5007), 809–817; Elrod-Erickson et al., (1996) *Structure* 4(10), 1171–1180; Isalan et al., (1997) *Proc Natl Acad Sci USA* 94(11), 5617–5621].

Selection of the previously reported phage display library for zinc finger domains binding to 5' nucleotides other than guanine or thymine met with no success, due to the cross-subsite interaction from aspartate in position 2 of the finger-3 recognition helix RSD-E-LKR. To extend the availability of zinc finger domains for the construction of artificial transcription factors, domains specifically recognizing the 5'-ANN-3' type of DNA sequences were selected. Other groups have described a sequential selection method which led to the characterization of domains recognizing four 5'-ANN-3' subsites, 5'-AAA-3', 5'-AAG-3', 5'-ACA3', and 5'-ATA-3' [Greisman et al., (1997) *Science* 275(5300), 657–661, Wolfe et al., (1999) *J Mol Biol* 285(5), 1917–1934]. The present disclosure uses a different approach to select zinc finger domains recognizing such sites by eliminating the target site overlap. First, finger 3 of C7 (RSD-E-RKR) (SEQ ID NO: 3) binding to the subsite 5'-GCG-3' was exchanged with a domain which did not contain aspartate in position 2 (FIG. 1). The helix TSG-N-LVR (SEQ ID NO: 6), previously characterized in finger 2 position to bind with high specificity to the triplet 5'-GAT-3', seemed a good candidate. This 3-finger protein (C7.GAT; FIG. 1A, lower panel), containing finger 1 and 2 of C7 and the 5'-GAT-3'-recognition helix in finger-3 position, was analyzed for DNA-binding specificity on targets with different finger-2 subsites by multi-target ELISA in comparison with the original C7 protein (C7.GCG; FIG. 1B). Both proteins bound to the 5'-TGG-3' subsite (note that C7.GCG binds also to 5'-GGG-3' due to the 5' specification of thymine or guanine by $Asp^2$ of finger 3 which has been reported earlier.

The recognition of the 5' nucleotide of the finger-2 subsite was evaluated using a mixture of all 16 5'-XNN-3' target sites (X=adenine, guanine, cytosine or thymine). Indeed, while the original C7. GCG protein specified a guanine or thymine in the 5' position of finger 2, C7.GAT did not specify a base, indicating that the cross-subsite interaction to the adenine complementary to the 5' thymine was abolished. A similar effect has previously been reported for variants of Zif268 where $Asp^2$ was replaced by $Ala^2$ by site-directed mutagenesis [Isalan et al., (1997) *Proc Natl Acad Sci USA* 94(11), 5617–5621; Dreier et al., (2000) *J. Mol. Biol.* 303, 489–502]. The affinity of C7.GAT, measured by gel mobility shift analysis, was found to be relative low, about 400 nM compared to 0.5 nM for C7.GCG [Segal et al., (1999) *Proc Natl Acad Sci USA* 96(6), 2758–2763], which may in part be due to the lack of the $Asp^2$ in finger 3.

Based on the 3-finger protein C7.GAT, a library was constructed in the phage display vector pComb3H [Barbas et al., (1991) *Proc. Natl. Acad. Sci. USA* 88, 7978–7982; Rader et al., (1997) *Curr. Opin. Biotechnol.* 8(4), 503–508]. Randomization involved positions-1, 1, 2, 3, 5, and 6 of the α-helix of finger 2 using a VNS codon doping strategy (V=adenine, cytosine or guanine, N=adenine, cytosine, guanine or thymine, S=cytosine or guanine). This allowed 24 possibilities for each randomized amino acid position, whereas the aromatic amino acids Trp, Phe, and Tyr, as well as stop codons, were excluded in this strategy. Because Leu is predominately found in position 4 of the recognition helices of zinc finger domains of the type $Cys_2$-$His_2$ this position was not randomized. After transformation of the library into ER2537 cells (New England Biolabs) the library contained $1.5 \times 10^9$ members. This exceeded the necessary library size by 60-fold and was sufficient to contain all amino acid combinations.

Six rounds of selection of zinc finger-displaying phage were performed binding to each of the sixteen 5'-GAT-ANN-GCG-3' biotinylated hairpin target oligonucleotides, respectively, in the presence of non-biotinylated competitor DNA. Stringency of the selection was increased in each round by decreasing the amount of biotinylated target oligonucleotide and increasing amounts of the competitor oligonucleotide mixtures. In the sixth round the target concentration was usually 18 nM, 5'-CNN-3',5'-GNN-3', and 5'-TNN-3' competitor mixtures were in 5-fold excess for each oligonucleotide pool, respectively, and the specific 5'-ANN-3' mixture (excluding the target sequence) in 10-fold excess. Phage binding to the biotinylated target oligonucleotide was recovered by capture to streptavidin-coated magnetic beads.

Clones were usually analyzed after the sixth round of selection. The amino acid sequences of selected finger-2 helices were determined and generally showed good conservation in positions-1 and 3 (FIG. 2), consistent with previously observed amino acid residues in these positions [Segal et al., (1999) *Proc Natl Acad Sci USA* 96(6), 2758–2763]. Position-1 was Gln when the 3' nucleotide was adenine, with the exception of domains binding 5'-ACA-3' (SPA-D-LTN) (SEQ ID NO: 77) where a Ser was strongly selected. Triplets containing a 3' cytosine selected $Asp^{-1}$ (exceptions were domains binding 5'-AGC-3' and 5'-ATC-3'), a 3' guanine $Arg^{-1}$, and a 5' thymine $Thr^{-1}$ and $His^{-1}$. The recognition of a 3' thymine by $His^{-1}$ has also been observed in finger 1 of TKK binding to 5'-GAT-3' (HIS-N-FCR) (SEQ ID NO: 78); [Fairall et al., (1993) *Nature (London)* 366 (6454), 483–7]). For the recognition of a middle adenine, Asp and Thr were selected in position 3 of the recognition helix. For binding to a middle cytosine, an $Asp^3$ or $Thr^3$ was selected, for a middle guanine, $His^3$ (an exception was recognition of 5'-AGT-3', which may have a different binding mechanism due to the unusual amino acid residue $His^{-1}$) and for a middle thymine, $Ser^3$ and $Ala^3$. Note also that the domains binding to 5'-ANG-3' subsites contain Asp$^2$ which likely stabilizes the interaction of the 3-finger protein by contacting the complementary cytosine of the 5' guanine in the finger-1 subsite. Even though there was a predominant selection of Arg and Thr in position 5 of the recognition helices, positions 1, 2 and 5 were variable.

The most interesting observation was the selection of amino acid residues in position 6 of the α-helices that determines binding to the 5' nucleotide of a 3 bp subsite. In contrast to the recognition of a 5' guanine, where the direct base contact is achieved by Arg or Lys in position 6 of the helix, no direct interaction has been observed in protein/DNA complexes for any other nucleotide in the 5' position [Elrod-Erickson et al., (1996) *Structure* 4(10), 1171–1180; Pavletich et al., (1993) *Science (Washington, D.C.,* 1883-) 261(5129), 1701–7; Kim et al., (1996) *Nat Struct Biol* 3(11), 940–945; Fairall et al., (1993) *Nature (London)* 366(6454), 483–7; Houbaviy et al., (1996) *Proc Natl Acad Sci USA* 93(24), 13577–82; Wuttke et al., (1997) *J Mol Biol* 273(1), 183–206; Nolte et al., (1998) *Proc Natl Acad Sci USA* 95(6), 2938–2943]. Selection of domains against finger-2 subsites of the type 5'-GNN-3' had previously generated domains containing only Arg$^6$ which directly contacts the 5' guanine [Segal et al., (1999) *Proc Natl Acad Sci USA* 96(6), 2758–2763]. However, unlike the results for 5'-GNN-3' zinc finger domains, selections of the phage display library against finger-2 subsites of the type 5'-ANN-3' identified domains containing various amino acid residues: Ala$^6$, Arg$^6$, Asn$^6$, Asp$^6$, Gln$^6$, Glu$^6$, Thr$^6$ or Val$^6$ (FIG. 2). In addition, one domain recognizing 5'-TAG-3' was selected from this library with the amino acid sequence RED-N-LHT (FIG. 3z) (SEQ ID NO: 71). Thr$^6$ is also present in finger 2 of Zif268 (RSD-H-LTT) (SEQ ID NO: 79) binding 5'-TGG-3' for which no direct contact was observed in the Zif268/DNA complex.

Finger-2 variants of C7.GAT were subcloned into bacterial expression vector as fusion with maltose-binding protein (MBP) and proteins were expressed by induction with 1 mM IPTG (proteins (p) are given the name of the finger-2 subsite against which they were selected). Proteins were tested by enzyme-linked immunosorbant assay (ELISA) against each of the 16 finger-2 subsites of the type 5'-GAT ANN GCG-3' to investigate their DNA-binding specificity (FIG. 3, black bars). In addition, the 5'-nucleotide recognition was analyzed by exposing zinc finger proteins to the specific target oligonucleotide and three subsites which differed only in the 5'-nucleotide of the middle triplet. For example, pAAA was tested on 5'-AAA-3', 5'-CAA-3', 5'-GAA-3', and 5'-TAA-3'subsites (FIG. 3, white bars). Many of the tested 3-finger proteins showed exquisite DNA-binding specificity for the finger-2 subsite against they were selected. Binding properties of domains which were boxed in FIG. 2 and are considered the most specific binders of each set are represented in the upper panel of FIG. 3, while additional domains tested (marked with an asterisk in FIG. 2) are summarized in the lower panel of FIG. 3. The exception were pAGC and pATC whose DNA binding was too weak to be detected by ELISA. The most promising helix for pAGC (DAS-H-LHT) (SEQ ID NO: 80) which contained the expected amino acid Asp-$^{-1}$ and His$^3$ specifying a 3' cytosine and middle guanine, but also a Thr$^6$ not selected in any other case for a 5' adenine, was analyzed without detectable DNA binding.

Figure 3A:
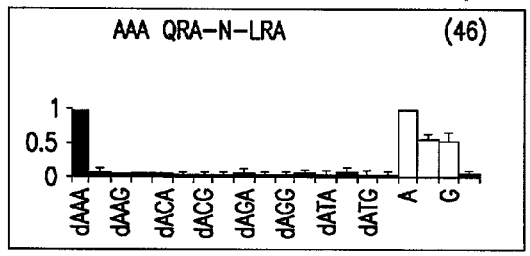
FIG. 3 (shown in 26 panels: 3a–3z) shows multitarget specificity assay to study DNA-binding properties of selected domains. At the top of each graph is the amino acid sequence of the finger-2 domain (positions-2 to 6 with respect to the helix start) of the 3-finger protein analyzed. Black bars represent binding to target oligonucleotides with different finger-2 subsites: AAA, AAC, AAG, AAT, ACA, ACC, ACG, ACT, AGA, AGC, AGT, ATA, ATC, ATG, and ATT. White bars represent binding to a set of oligonucleotides where the finger-2 subsite only differs in the 5' position, for example for the domain binding the 5'-AAA-3' subsite (FIG. 3a) AAA, CAA, GAA, or TAA to evaluate the 5' recognition. The height of each bar represents the relative affinity of the protein for each target, averaged over two independent experiments and normalized to the highest signal among the black or white bars. Error bars represent the deviation from the average. Proteins analyzed correspond to the boxed helix sequences from FIG. 2. *: Proteins containing a finger-2 domain which was generated by site-directed mutagenesis.
Figure 3B:
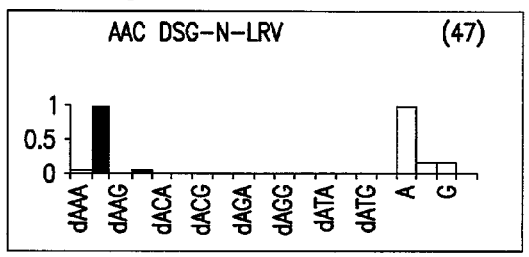
Figure 3C:
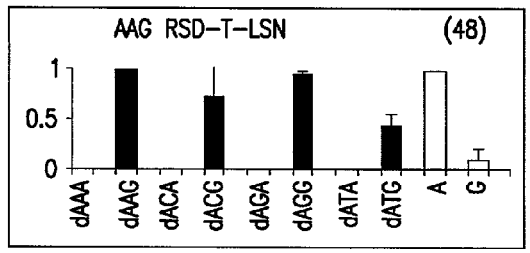
Figure 3D:
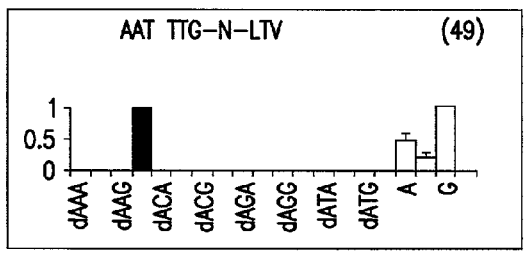
Figure 3E:
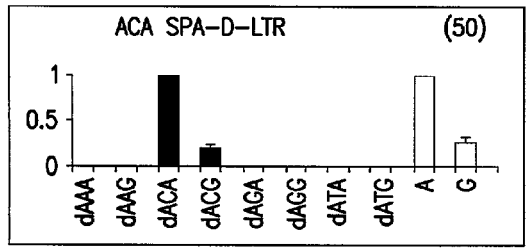
Figure 3F:
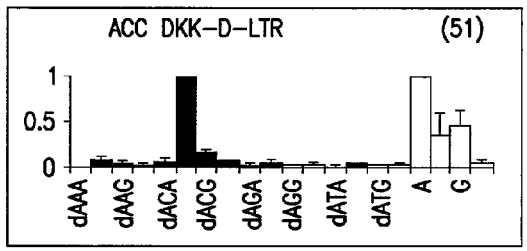
Figure 3G:
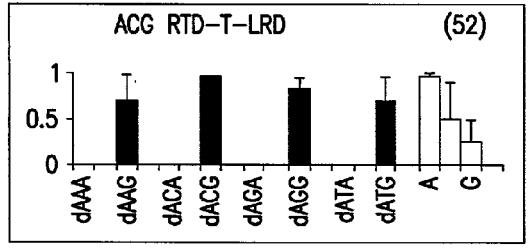
Figure 3H:
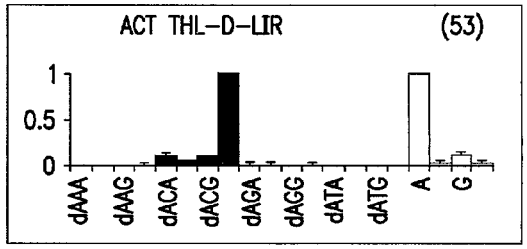
Figure 3I:
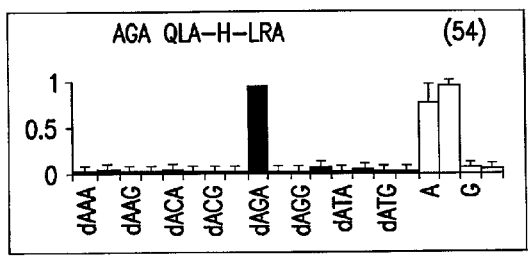

To analyze a larger set, the pool of coding sequences for pAGC was subcloned into the plasmid pMal after the sixth round of selection and 18 individual clones were tested for DNA-binding specificity, of which none showed measurable DNA-binding in ELISA. In the case of pATC, two helices (RRS-S-CRK and RRS-A-CRR) (SEQ ID NOs: 80, 81) were selected containing a Leu$^4$ to Cys$^4$ mutation, for which no DNA binding was detectable. Rational design was applied to find domains binding to 5'-AGC-3' or 5'-ATC-3', since no proteins binding these finger-2 subsites were generated by phage display. Finger-2 mutants were constructed based on the recognition helices which were previously demonstrated to bind specifically to 5'-GGC-3' (ERS-K-LAR (SEQ ID NO: 82), DPG-H-LVR (SEQ ID NO: 83)) and 5'-GTC-3' (DPG-A-LVR) (SEQ ID NO: 84) [Segal et al., (1999) *Proc Natl Acad Sci USA* 96(6), 2758–2763]. For pAGC two proteins were constructed (ERS-K-LRA (SEQ ID NO: 85), DPG-H-LRV (SEQ ID NO: 86)) by simply exchanging position 5 and 6 to a 5' adenine recognition motif RA or RV (FIGS. 3a, 3b and 3i). DNA binding of these proteins was below detection level. In the case of pATC two finger-2 mutants containing a RV motif (FIG. 3b) were constructed (DPG-A-LRV (SEQ ID NO: 87), DPG-S-LRV (SEQ ID NO: 88)). Both proteins bound DNA with extremely low affinity regardless if position 3 was Ala or Ser.

Figure 3J:
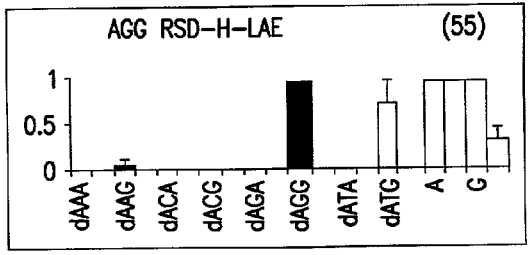
Figure 3K:
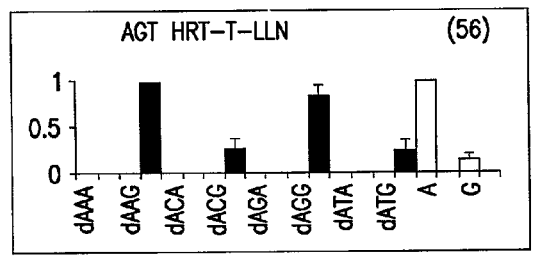
Figure 3L:
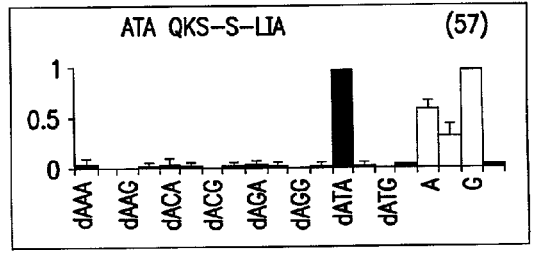
Figure 3M:
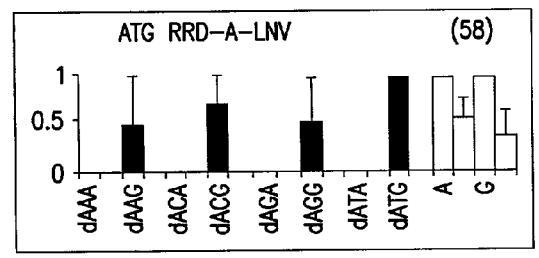
Figure 3N:
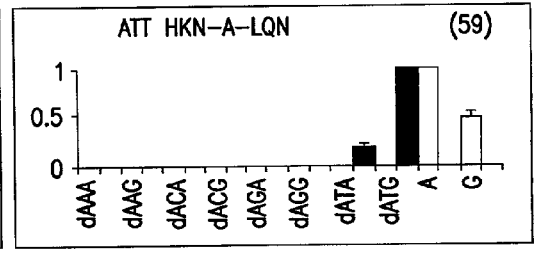
Figure 3O:
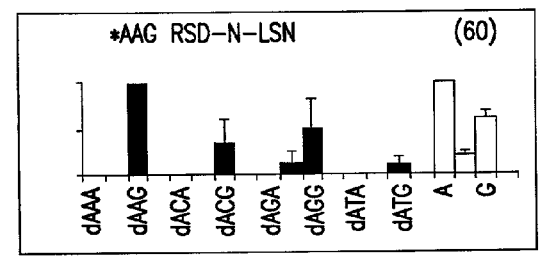
Figure 3P:
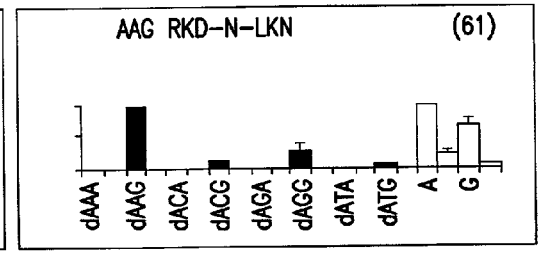
Figure 3Q:
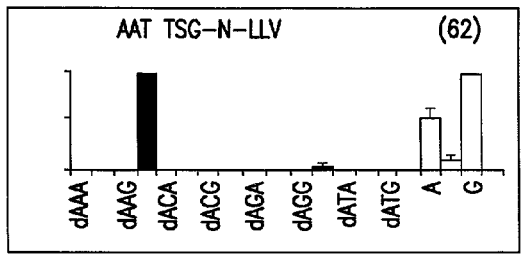
Figure 3R:
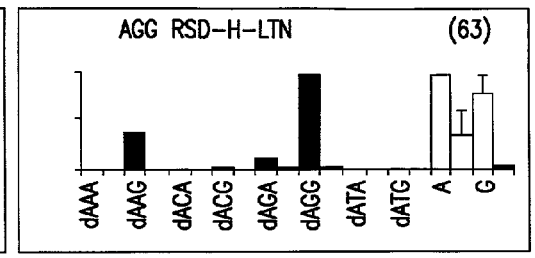

Analysis of the 3-finger proteins on the sixteen finger-2 subsites by ELISA revealed that some finger-2 domains bound best to a target they were not selected against. First, the predominantly selected helix for 5'-AGA-3' was RSD-H-LTN (SEQ ID NO: 63), which in fact bound 5'-AGG-3' (FIG. 3r). This can be explained by the Arg in position-1. In addition, this protein showed a better discrimination of a 5' adenine compared to the predominantly selected helix pAGG (RSD-H-LAE (SEQ ID NO: 55); FIG. 3j). Second, a helix binding specifically to 5'-AAG-3' (RSD-N-LKN (SEQ ID NO: 61); FIG. 3p) was actually selected against 5'-AAC-3' (FIG. 2), and bound more specific to the finger-2 subsite 5'-AAG-3' than PAAG (RSD-T-LSN (SEQ ID NO: 48); FIG. 3c), which had been selected in the 5'-AAG-3' set. In addition, proteins directed to target sites of the type 5'-ANG-3' showed cross reactivity with all four target sites of the type 5'-ANG-3', except for pAGG (FIG. 3j and 3r). The recognition of a middle purine seems more restrictive than of a middle pyrimidine, because also pAAG (RSD-N-LKN (SEQ ID NO: 61); FIG. 3p) had only moderate cross-reactivity.

Figure 3S:
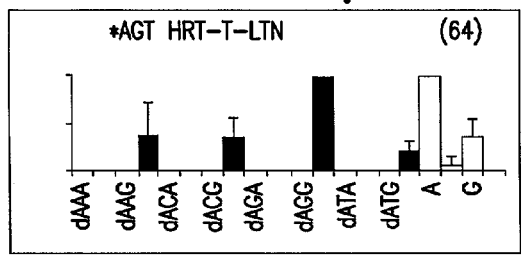

In comparison, the proteins pACG (RTD-T-LRD (SEQ ID NO: 52); FIG. 3g) and pATG (RRD-A-LNV (SEQ ID NO: 58); FIG. 3m) show cross-reactivity with all 5'-ANG-3' subsites. The recognition of a middle pyrimidine has been reported to be difficult in previous studies for domains binding to 5'-GNG-3' DNA sequences [Segal et al., (1999) *Proc Natl Acad Sci USA* 96(6), 2758–2763; Dreier et al., (2000) *J. Mol. Biol.* 303, 489–502]. To improve the recognition of the middle nucleotide, finger-2 mutants containing different amino acid residues in position 3 were generated by site-directed mutagenesis. Binding of pAAG (RSD-T-LSN (SEQ ID NO: 48), FIG. 3c) was more specific for a middle adenine after a Thr$^3$ to Asn$^3$ mutation (FIG. 3o). The binding to 5'-ATG-3' (SRD-A-LNV (SEQ ID NO: 58); FIG. 3m) was improved by a single amino acid exchange Ala$^3$ to Gln$^3$ (FIG. 3w), while a Thr$^3$ to Asp$^3$ or Gln$^3$ mutation for pACG (RSD-T-LRD (SEQ ID NO: 52); FIG. 3g) abolished DNA binding. In addition, the recognition helix pAGT (HRT-T-LLN (SEQ ID NO: 56); FIG. 3k) showed cross-reactivity for the middle nucleotide which was reduced by a Leu$^5$ to Thr$^5$ substitution (FIG. 3s). Surprisingly, improved discrimination for the middle nucleotide was often associated with some loss of specificity for the recognition of the 5' adenine (compare FIG. 3o-3p, 3m-3w, 3k-3s).

Selection of zinc finger domains binding to subsites containing a 5' adenine or cytosine from the previously described finger-2 library based on the 3-finger protein C7 [Segal et al., (1999) *Proc Natl Acad Sci USA* 96(6), 2758–2763] was not suitable for the selection of zinc-finger domains due to the limitation of aspartate in position 2 of finger 3 which makes a cross-subsite contact to the nucleotide complementary of the 5' position of the finger-2 subsite (FIG. 1a, upper panel). We eliminated this contact by exchanging finger 3 with a domain lacking Asp$^2$ (FIG. 1b). Finger 2 of C7.GAT was randomized and a phage display library constructed. In most cases, novel 3-finger proteins were selected binding to finger-2 subsites of the type 5'-ANN-3'. For the subsites 5'-AGC-3' and 5'-ATC-3' no tight binders were identified. This was not expected, because the domains binding to the subsite 5'-GGC-3' and 5'-GTC-3' previously selected from the C7-based phage display library showed excellent DNA-binding specificity and affinity of 40 nM to their target site [Segal et al., (1999) *Proc Natl Acad Sci USA* 96(6), 2758–2763]. One simple explanation would be the limiting randomization strategy by the usage of VNS codons which do not include the aromatic amino acid residues. These were not included in the library, because for the domains binding to 5'-GNN-3' subsites no aromatic amino acid residues were selected, even though they were included in the randomization strategy [Segal et al., (1999) *Proc Natl Acad Sci USA* 96(6), 2758–2763]. However, there have been zinc finger domains reported containing aromatic residues, like finger 2 of CFII2 (VKD-Y-LTK (SEQ ID NO: 89); [Gogos et al., (1996) *PNAS* 93, 2159–2164]), finger 1 of TFIIIA (KNW-K-LQA (SEQ ID NO: 90; [Wuttke et al., (1997) *J Mol Biol* 273(1), 183–206]), finger 1 of TTK (HIS-N-FCR (SEQ ID NO: 78); [Fairall et al., (1993) *Nature (London)* 366(6454), 483–7]) and finger 2 of GLI (AQ Y-M-LVV (SEQ ID NO: 91); [Pavletich et al., (1993) *Science (Washington, D.C.,* 1883-) 261(5129), 1701–7]). Aromatic amino acid residues might be important for the recognition of the subsites 5'-AGC-3' and 5'-ATC-3'.

In recent years it has become clear that the recognition helix of $Cys_2$-$His_2$ zinc finger domains can adopt different orientations relative to the DNA in order to achieve optimal binding [Pabo et al., (2000) *J. Mol. Biol.* 301, 597–624]. However, the orientation of the helix in this region may be partially restricted by the frequently observed interaction involving the zinc ion, His$^7$, and the phosphate backbone. Furthermore, comparison of binding properties of interactions in protein/DNA complexes have led to the conclusion that the Ca atom of position 6 is usually 8.8±0.8 Å apart from the nearest heavy atom of the 5' nucleotide in the DNA subsite, which favors only the recognition of a 5' guanine by Arg$^6$ or Lys$^6$ [Pabo et al., (2000) *J. Mol. Biol.* 301, 597–624]. To date, no interaction of any other position 6 residue with a base other than guanine has been observed in protein/DNA complexes. For example, finger 4 of YY1 (QST-N-LKS) (SEQ ID NO: 92) recognizes 5'-CAA-3' but there was no contact observed between Ser$^6$ and the 5' cytosine [Houbaviy et al., (1996) *Proc Natl Acad Sci USA* 93(24), 13577–82]. Further, in the case of Thr$^6$ in finger 3 of YY1 (LDF-N-LRT) (SEQ ID NO: 93), recognizing 5'-ATT-3', and in finger 2 of Zif268 (RSD-H-LTT) (SEQ ID NO: 79), specifying 5'-T/GGG-3', no contact with the 5' nucleotide was observed [Houbaviy et al., (1996) *Proc Natl Acad Sci USA* 93(24), 13577–82; Elrod-Erickson et al., (1996) *Structure* 4(10), 1171–1180]. Finally, Ala$^6$ of finger 2 of tramtrack (RKD-N-MTA) (SEQ ID NO: 94) binding to the subsite 5'-AAG-3' does not contact the 5' adenine [Fairall et al., (1993) *Nature (London)* 366(6454), 483–7].

Amino acid residues Ala$^6$, Val$^6$, Asn$^6$ and even Arg$^6$, which in a different context was demonstrated to bind a 5' guanine efficiently [Segal et al., (1999) *Proc Natl Acad Sci USA* 96(6), 2758–2763], were predominantly selected from the C7.GAT library for DNA subsites of the type 5'-ANN-3' (FIG. 2). In addition, position 6 was selected as Thr, Glu and Asp depending on the finger-2 target site. This is consistent with early studies from other groups where positions of adjacent fingers were randomized [Jamieson et al., (1996) *Proc Natl Acad Sci USA* 93, 12834–12839; Isalan et al., (1998) *Biochemistry* 37(35), 12026–12033]. Screening of phage display libraries had resulted in selection of amino acid residues Tyr, Val, Thr, Asn, Lys, Glu and Leu, as well as Gly, Ser and Arg, but not Ala, for the recognition of a 5' adenine. In addition, using a sequential phage display selection strategy several domains binding to 5'-ANN-3' subsites were identified and specificity evaluated by target site selections. Arg, Ala and Thr in position 6 of the helix were demonstrated to recognize predominantly a 5' adenine [Wolfe et al., (1999) *Annu. Rev. Biophys. Biomol. Struct.* 3, 183–212].

In addition, Thr$^6$ specifies a 5' adenine as shown by target site selection for finger 5 of Gfi-1 (QSS-N-LIT) (SEQ ID NO: 95) binding to the subside 5'-AAA-3' [Zweidler-McKay et al., (1996) *Mol. Cell. Biol.* 16(8), 4024–4034]. These examples, including the present results, indicate that there is likely a relation between amino acid residue in position 6 and the 5' adenine, because they are frequently selected. This is at odds with data from crystallographic studies, that never showed interaction of position 6 of the α-helix with a 5' nucleotide except guanine. One simple explanation might be that short amino acid residues, like Ala, Val, Thr, or Asn are not a sterical hindrance in the binding mode of domains recognizing 5'-ANN-3' subsites. This is supported by results gathered by site-directed mutagenesis in position 6 for a helix (QRS-A-LTV) (SEQ ID NO: 96) binding to a 5'-G/ATA-3' subsite [Gogos et al., (1996) *PNAS* 93, 2159–2164]. Replacement of Val$^6$ with Ala$^6$, which were also found for domains described here, or Lys$^6$, had no affect on the binding specificity or affinity.

Computer modeling was used to investigate possible interactions of the frequently selected Ala$^6$, Asn$^6$ and Arg$^6$ with a 5' adenine. Analysis of the interaction from Ala$^6$ in the helix binding to 5'-AAA-3' (QRA-N-LRA; FIG. 3a) (SEQ ID NO: 46) with a 5' adenine was based on the coordinates of the protein/DNA complex of finger 1 (QSG-S-LTR) (SEQ ID NO: 97) from a Zif268 variant. If Gln$^{-1}$ and Asn$^3$ of QRA-N-LRA (SEQ ID NO: 98) hydrogen bond with their respective adenine bases in the canonical way, these interactions should fix a distance of about 8 Å between the methyl group of Ala$^6$ and the 5' adenine and more than 11 Å between the methyl groups of Ala$^6$ and the thymine base-paired to the adenine, suggesting also that no direct contact can be proposed for Val$^6$ and Thr$^6$.

Interestingly, the expected lack of 5' specificity by short amino acids in position 6 of the α-helix is only partially supported by the binding data. Helices such as RRD-A-LN V (SEQ ID NO: 58) (FIG. 3m) and the finger-2 helix RSD-H-LTT (SEQ ID NO: 5) of C7.GAT (FIG. 1B, lower panel) did indeed show essentially no 5' specificity. However, helix DSG-N-LRV (SEQ ID NO: 47) (FIG. 3b) displayed excellent specificity for a 5' adenine, while TSH-G-LTT (SEQ ID NO: 70) (FIG. 3y) was specific for 5' adenine or guanine. Other helices with short position-6 residues displayed varying degrees of 5' specificity, with the only obvious consistency being that 5' thymine was usually excluded (FIG. 3). Since it is unlikely that the position-6 residue can make a direct contribution to specificity, the observed binding patterns must derive from another source. Possibilities include local sequence-specific DNA structure and overlapping interactions from neighboring domains. The latter possibility is disfavored, however, because the residue in position 2 of finger 3 (which is frequently observed to contact the neighboring site) is glycine in the parental protein C7.GAT, and because 5' thymine was not excluded by the two helices mentioned above.

Asparagine was also frequently selected in position 6. Helix HRT-T-LTN (SEQ ID NO: 56) (FIG. 3k) and RSD-T-LSN (SEQ ID NO: 48) (FIG. 3c) displayed excellent specificity for 5' adenine. However, Asn$^6$ also seemed to impart specificity for both adenine and guanine (FIGS. 3n, 3p and 3r), suggesting an interaction with the N7 common to both nucleotides. Computer modeling of the helix binding to 5'-AGG-3' (RSD-H-LTN (SEQ ID NO: 90); FIG. 3r), based on the coordinates of finger 2, binding to 5'-TGG-3', in the Zif268/DNA crystal structure (RSD-H-LTT(SEQ ID NO: 79); [Elrod-Erickson et al., (1996) *Structure* 4(10), 1171–1180]), suggested that the Nd of Asn6 would be approximately 4.5 Å from N7 of the 5' adenine. A modest reorientation of the α-helix which is considered within the range of canonical docking orientations [Pabo et al., (2000) *J. Mol. Biol.* 301, 597–624], could plausibly bring the Nd within hydrogen bonding distance, analogous to the reorientation observed when glutamate rather than arginine appears in position-1. However, it is interesting to speculate why Asn$^6$ was selected in this 5'-ANN-3' recognition set while the longer Gln$^6$ was not. Gln$^6$, being more flexible, may have been able to stabilize other interactions that were selected against during phage display. Alternatively, the shorter side chain of Asn$^6$ might accommodate an ordered water molecule that could contact the 5' nucleotide without reorientation of the helix.

Figure 3T:
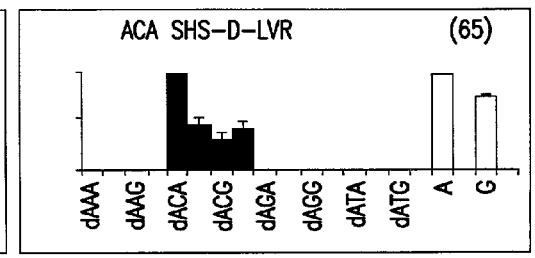
Figure 3U:
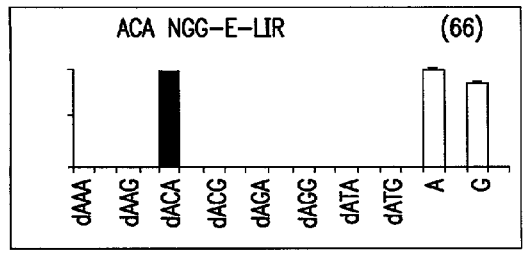
Figure 3V:
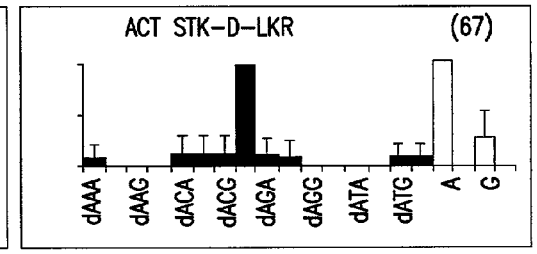
Figure 3W:
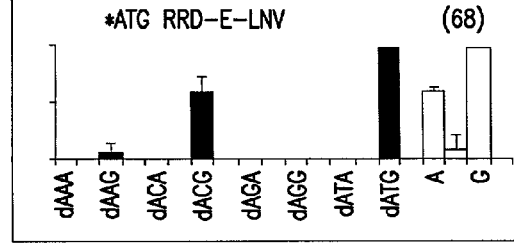
Figure 3X:
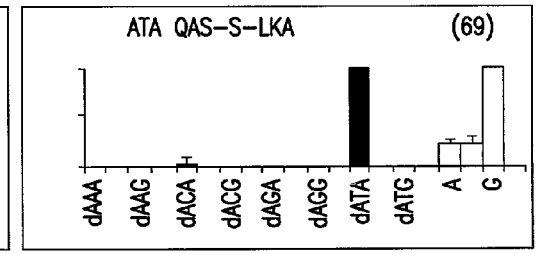
Figure 3Y:
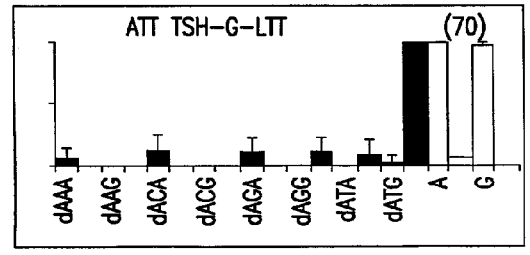
Figure 3Z:
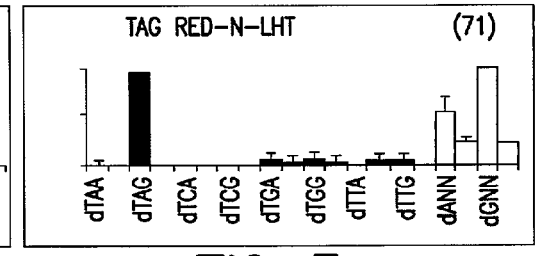

The final residue to be considered is Arg$^6$. It was somewhat surprising that Arg$^6$ was selected so frequently on 5'-ANN-3' targets because in our previous studies, it was unanimously selected to recognize a 5' guanine with high specificity [Segal et al., (1999) *Proc Natl Acad Sci USA* 96(6), 2758–2763]. However, in the current study, Arg$^6$ primarily specified 5' adenine (FIGS. 3e, f, h and v), in some cases in addition to recognition of a 5' guanine (FIGS. 3t and u). Computer modeling of helix binding to 5'-ACA-3' (SPA-D-LTR (SEQ ID NO: 50); FIG. 3e), based on the coordinates of finger 1 QSG-S-LTR (SEQ ID NO: 98) of a Zif268 variant binding 5'-GCA-3' [Elrod-Erickson et al., (1998) *Structure* 6(4), 451–464], suggested that Arg$^6$ could easily adopt a configuration that allowed it to make a cross-strand hydrogen bond to O4 of a thymine base-paired to 5' adenine. In fact, Arg$^6$ could bind with good geometry to both the O4 of thymine and O6 of a guanine base-paired to a middle cytosine. Such an interaction is consistent with the fact that Arg$^6$ was selected almost unanimously when the target sequence was 5'-ACN-3'. The expectation for arginine to facilitate multiple interactions is compelling. Several lysines in TFIIIA were observed by NMR to be conformationally flexible [Foster et al., (1997) *Nat. Struct. Biol.* 4(8), 605–608], and Gln$^{-1}$ behaves in a manner which suggests flexibility [Dreier et al., (2000) *J. Mol. Biol.* 303, 489–502]. Arginine has more rotable bonds and more hydrogen bonding potential than lysine or glutamine and it is attractive to speculate that Arg$^6$ is not limited to recognition of 5' guanine.

Amino acid residues in positions-1 and 3 were generally selected in analogy to their 5'-GNN-3' counterparts with two exceptions. His$^{-1}$ was selected for pAGT and pATT, recognizing a 3' thymine (FIGS. 3k, 3n and 3y), and Ser$^{-1}$ for pACA, recognizing a 3' adenine (FIGS. 3e and 3t). While Gln$^{-1}$ was frequently used to specify a 3' adenine in subsites of the type 5'GNN-3', a new element of 3' adenine recognition was suggested from this study involving Ser$^{-1}$ selected for domains recognizing the 5'-ACA-3' subsite (FIG. 2) which can make a hydrogen bond with the 3' adenine. Computer modeling demonstrates that Ala$^2$, co-selected in the helix SPA-D-LTR (SEQ ID NO: 50) (FIG. 3e), can potentially make a van der Waals contact with the methyl group of the thymine based-paired to 3' adenine. The best evidence that Ala$^2$ might be involved is that helix SP A-D-LTR (SEQ ID NO: 50) (FIG. 3e) is strongly specific for 3' adenine while SHS-D-LVR (SEQ ID NO: 65) (FIG. 3t) is not. Gln$^{-1}$ is often sufficient for 3' adenine recognition. However, data from our previous studies suggested that the side chain of Gln$^{-1}$ can adopt multiple conformations, enabling, for example, recognition of 3' thymine [Nardelli et al., (1992) *Nucleic Acids Res.* 20(16), 4137–44; Elrod-Erickson et al., (1998) *Structure* 6(4), 451–464; Dreier et al., (2000) *J. Mol. Biol.* 303, 489–502]. Ala$^2$ in combination with Ser$^{-1}$ may be an alternative means to specificity a 3' adenine.

Another interaction not observed in the 5'-GNN-3' study is the cooperative recognition of 3' thymine by His$^{-1}$ and the residue at position 2. In finger 1 of the crystal structure of the tramtrack/DNA complex, helix HIS-N-FCR (SEQ ID NO: 99) binds the subsite 5'-GAT-3' [Fairall et al., (1993) *Nature (London)* 366(6454), 483–7]. The His$^{-1}$ ring is perpendicular to the plane of the 3' thymine base and is approximately 4 Å from the methyl group. Ser$^2$ additionally makes a hydrogen bond with O4 of 3' thymine. A similar set of contacts can be envisioned by computer modeling for the recognition of 5'-ATT-3' by helix HKN-A-LQN (SEQ ID NO: 100) (FIG. 3n). Asn$^2$ in this helix has the potential not only to hydrogen bond with 3' thymine but also with the adenine base-paired to thymine. His$^{-1}$ was also found for the helix binding 5'-AGT-3' (HRT-T-LLN (SEQ ID NO: 98); FIG. 3k) in combination with a Thr$^2$. Thr is structurally similar to Ser and might be involved in a similar recognition mechanism.

In conclusion, the results of the characterization of zinc finger domains reported in this study binding 5'-ANN-3' DNA subsites is consistent with the overall view that there is no general recognition code, which makes rational design of additional domains difficult. However, phage display selections can be applied and pre-defined zinc finger domains can serve as modules for the construction of artificial transcription factors. The domains characterized here enables targeting of DNA sequences other than 5'-(GNN)$_6$-3'. This is an important supplement to existing domains, since G/C-rich sequences often contain binding sites for cellular proteins and 5'(GNN)$_6$-3' sequences may not be found in all promoters.

II. Polynucleotides, Expression Vectors and Transformed Cells

The invention includes a nucleotide sequence encoding a zinc finger-nucleotide binding polypeptide. DNA sequences encoding the zinc finger-nucleotide binding polypeptides of the invention, including native, truncated, and expanded polypeptides, can be obtained by several methods. For example, the DNA can be isolated using hybridization procedures which are well known in the art. These include, but are not limited to: (1) hybridization of probes to genomic or cDNA libraries to detect shared nucleotide sequences; (2) antibody screening of expression libraries to detect shared structural features; and (3) synthesis by the polymerase chain reaction (PCR). RNA sequences of the invention can be obtained by methods known in the art (See, for example, *Current Protocols in Molecular Biology*, Ausubel, et al. Eds., 1989).

The development of specific DNA sequences encoding zinc finger-nucleotide binding polypeptides of the invention can be obtained by: (1) isolation of a double-stranded DNA sequence from the genomic DNA; (2) chemical manufacture of a DNA sequence to provide the necessary codons for the polypeptide of interest; and (3) in vitrosynthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA is the least common. This is especially true when it is desirable to obtain the microbial expression of mammalian polypeptides due to the presence of introns.

For obtaining zinc finger derived-DNA binding polypeptides, the synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the formation of cDNA sequences. Among the standard procedures for isolating cDNA sequences of interest is the formation of plasmid-carrying cDNA libraries which are derived from reverse transcription of MRNA which is abundant in donor cells that have a high level of genetic expression. When used in combination with polymerase chain reaction technology, even rare expression products can be clones. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucleic Acid Research* 11:2325, 1983).

A polypeptide of this invention can be operatively linked to one or more functional peptides. Such functional peptides are well known in the art and can be a transcription regulating factor such as a repressor or activation domain or a peptide having other functions. Exemplary and preferred such functional peptides are nucleases, methylases, nuclear localization domains, and restriction enzymes such as endo- or ectonucleases (See, e.g., Chandrasegaran and Smith, Biol. Chem., 380:841–848, 1999).

An exemplary repression domain peptide is the ERF repressor domain (ERD) (Sgouras, D. N., Athanasiou, M. A., Beal, G. J., Jr., Fisher, R. J., Blair, D. G. & Mavrothalassitis, G. J. (1995) *EMBO J.* 14, 4781–4793), defined by amino acids 473 to 530 of the ets2 repressor factor (ERF). This domain mediates the antagonistic effect of ERF on the activity of transcription factors of the ets family. A synthetic repressor is constructed by fusion of this domain to the—or C-terminus of the zinc finger protein. A second repressor protein is prepared using the Krüppel-associated box (KRAB) domain (Margolin, J. F., Friedman, J. R., Meyer, W., K. -H., Vissing, H., Thiesen, H. -J. & Rauscher III, F. J. (1994) *Proc. Natl. Acad. Sci. USA* 91, 4509–4513). This repressor domain is commonly found at the N-terminus of zinc finger proteins and presumably exerts its repressive activity on TATA-dependent transcription in a distance- and orientation-independent manner (Pengue, G. & Lania, L. (1996) *Proc. Natl. Acad. Sci. USA* 93, 1015–1020), by interacting with the RING finger protein KAP-1 (Friedman, J. R., Fredericks, W. J., Jensen, D. E., Speicher, D. W., Huang, X. -P., Neilson, E. G. & Rauscher III, F. J. (1996) *Genes & Dev.* 10, 2067–2078). We utilized the KRAB domain found between amino acids 1 and 97 of the zinc finger protein KOX1 (Margolin, J. F., Friedman, J. R., Meyer, W., K. -H., Vissing, H., Thiesen, H. -J. & Rauscher III, F. J. (1994) *Proc. Natl. Acad. Sci. USA* 91, 4509–4513). In this case an N-terminal fusion with a zinc-finger polypeptide is constructed. Finally, to explore the utility of histone deacetylation for repression, amino acids 1 to 36 of the Mad mSIN3 interaction domain (SID) are fused to the N-terminus of the zinc finger protein (Ayer, D. E., Laherty, C. D., Lawrence, Q. A., Armstrong, A. P. & Eisenman, R. N. (1996) *Mol. Cell. Biol.* 16, 5772–5781). This small domain is found at the N-terminus of the transcription factor Mad and is responsible for mediating its transcriptional repression by interacting with mSIN3, which in turn interacts the corepressor N-CoR and with the histone deacetylase mRPD1 (Heinzel, T., Lavinsky, R. M., Mullen, T. -M., Sšderstršm, M., Laherty, C. D., Torchia, J., Yang, W. -M., Brard, G., Ngo, S. D. & al., e. (1997) *Nature* 387, 43–46). To examine gene-specific activation, transcriptional activators are generated by fusing the zinc finger polypeptide to amino acids 413 to 489 of the herpes simplex virus VP16 protein (Sadowski, I., Ma, J., Triezenberg, S. & Ptashne, M. (1988) *Nature* 335, 563–564), or to an artificial tetrameric repeat of VP16's minimal activation domain, (Seipel, K., Georgiev, O. & Schaffner, W. (1992) *EMBO J.* 11, 4961–4968), termed VP64.

III. Pharmaceutical Compositions

In another aspect, the present invention provides a pharmaceutical composition comprising a therapeutically effective amount of a zinc finger-nucleotide binding polypeptide or a therapeutically effective amount of a nucleotide sequence that encodes a zinc finger-nucleotide binding polypeptide in combination with a pharmaceutically acceptable carrier.

As used herein, the terms "pharmaceutically acceptable", "physiologically tolerable" and grammatical variations thereof, as they refer to compositions, carriers, diluents and reagents, are used interchangeable and represent that the materials are capable of administration to or upon a human without the production of undesirable physiological effects such as nausea, dizziness, gastric upset and the like which would be to a degree that would prohibit administration of the composition.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, as well as pH buffering agents and the like which enhance the effectiveness of the active ingredient.

The therapeutic pharmaceutical composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes. Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

IV. Uses

In one embodiment, a method of the invention includes a process for modulating (inhibiting or suppressing) expression of a nucleotide sequence comprising a zinc finger-nucleotide binding motif, which method includes the step of contacting the zinc finger-nucleotide binding motif with an effective amount of a zinc finger-nucleotide binding polypeptide that binds to the motif. In the case where the nucleotide sequence is a promoter, the method includes inhibiting the transcriptional transactivation of a promoter containing a zinc finger-DNA binding motif. The term "inhibiting" refers to the suppression of the level of activation of transcription of a structural gene operably linked to a promoter, containing a zinc finger-nucleotide binding motif, for example. In addition, the zinc finger-nucleotide binding polypeptide derivative may bind a motif within a structural gene or within an RNA sequence.

The term "effective amount" includes that amount which results in the deactivation of a previously activated promoter or that amount which results in the inactivation of a promoter containing a zinc finger-nucleotide binding motif, or that amount which blocks transcription of a structural gene or translation of RNA. The amount of zinc finger derived-nucleotide binding polypeptide required is that amount necessary to either displace a native zinc finger-nucleotide binding protein in an existing protein/promoter complex, or that amount necessary to compete with the native zinc finger-nucleotide binding protein to form a complex with the promoter itself. Similarly, the amount required to block a structural gene or RNA is that amount which binds to and blocks RNA polymerase from reading through on the gene or that amount which inhibits translation, respectively. Preferably, the method is performed intracellularly. By functionally inactivating a promoter or structural gene, transcription or translation is suppressed. Delivery of an effective amount of the inhibitory protein for binding to or "contacting" the cellular nucleotide sequence containing the zinc finger-nucleotide binding protein motif, can be accomplished by one of the mechanisms described herein, such as by retroviral vectors or liposomes, or other methods well known in the art.

The term "modulating" refers to the suppression, enhancement or induction of a function. For example, the zinc finger-nucleotide binding polypeptide of the invention may modulate a promoter sequence by binding to a motif within the promoter, thereby enhancing or suppressing transcription of a gene operatively linked to the promoter nucleotide sequence. Alternatively, modulation may include inhibition of transcription of a gene where the zinc finger-nucleotide binding polypeptide binds to the structural gene and blocks DNA dependent RNA polymerase from reading through the gene, thus inhibiting transcription of the gene. The structural gene may be a normal cellular gene or an oncogene, for example. Alternatively, modulation may include inhibition of translation of a transcript.

The promoter region of a gene includes the regulatory elements that typically lie 5' to a structural gene. If a gene is to be activated, proteins known as transcription factors attach to the promoter region of the gene. This assembly resembles an "on switch" by enabling an enzyme to transcribe a second genetic segment from DNA to RNA. In most cases the resulting RNA molecule serves as a template for synthesis of a specific protein; sometimes RNA itself is the final product.

The promoter region may be a normal cellular promoter or, for example, an onco-promoter. An onco-promoter is generally a virus-derived promoter. For example, the long terminal repeat (LTR) of retroviruses is a promoter region which may be a target for a zinc finger binding polypeptide variant of the invention. Promoters from members of the Lentivirus group, which include such pathogens as human T-cell lymphotrophic virus (HTLV) 1 and 2, or human immunodeficiency virus (HIV) 1 or 2, are examples of viral promoter regions which may be targeted for transcriptional modulation by a zinc finger binding polypeptide of the invention.

To investigate whether the domains described here specifically binding to 5'-ANN-3' DNA sequences are suitable for the construction of such artificial transcription factors, four 6-finger proteins were assembled containing various numbers of 5'-ANN-3' domains. For each of the 6-finger proteins two 3 finger-coding regions were generated by PCR overlap extension using the Sp1C framework [Beerli et al., (1998) Proc Natl Acad Sci USA 95(25), 14628–14633]. These 3-finger proteins were then fused to create 6-finger proteins via restriction sites (FIG. 4a) and cloned into the bacterial expression vector pMal for analysis of DNA-binding specificity and affinity. First, the 6-finger protein pAart was constructed, designed to recognize the arbitrary 18 bp target site 5'-ATG-TAG-AGA-AAA-ACC-AGG-3', which was completely free of 5'-GNN-3' triplets. Secondly, three 6-finger proteins containing both, 5'-GNN-3' and 5'-ANN-3' domains, were constructed. The well characterized model of the erbB-2 and erbB-3 genes for which we have previously shown that regulation of the endogenous gene was specifically achieved by, respectively, the 6-finger protein pE2C or pE3, which bound to 5'-(GNN)$_6$-3' DNA sequences [Beerli et al., (2000) Proc Natl Acad Sci USA 97(4), 1495–1500; Beerli et al., (2000) J. Biol. Chem. 275(42), 32617–32627] were chosen for study.

Figure 4B:
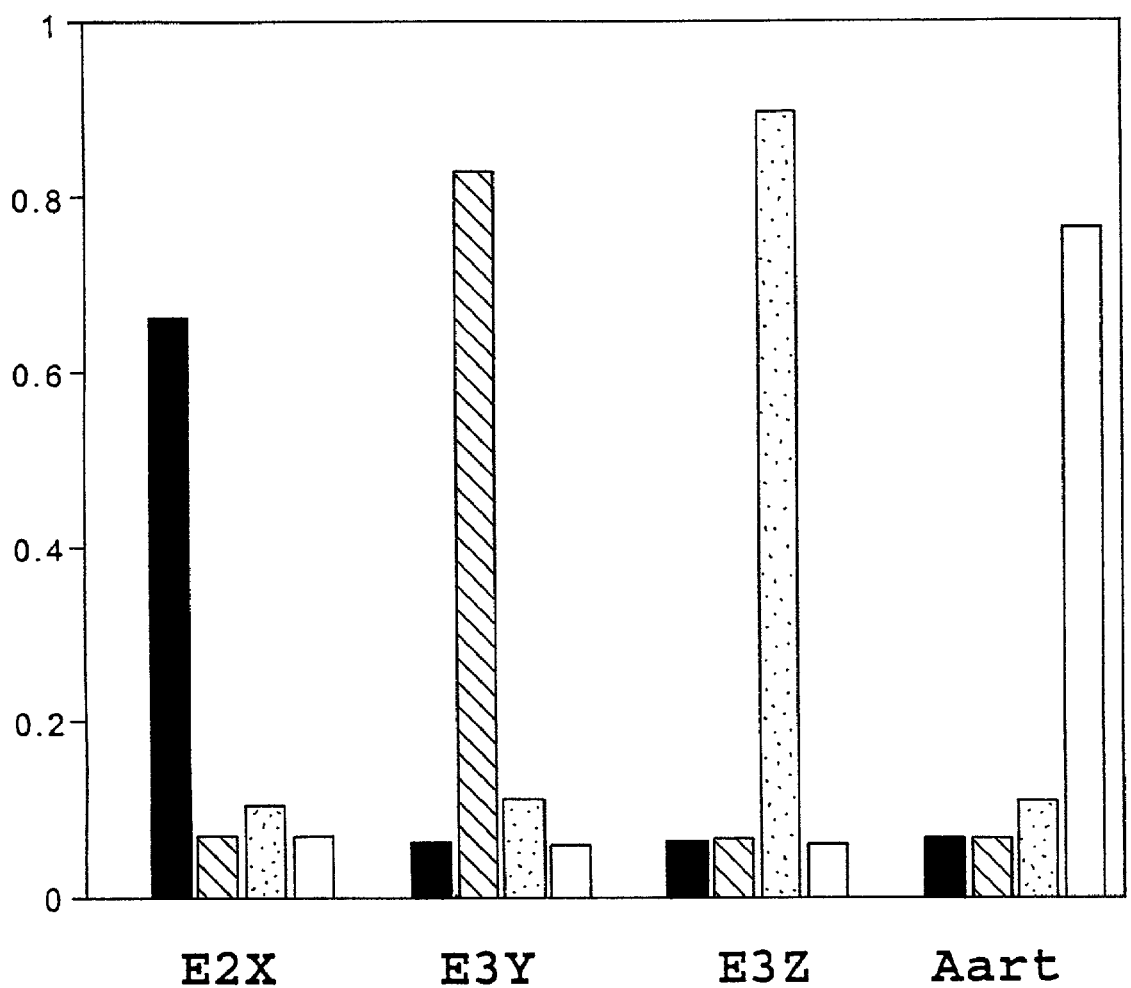
FIG. 4 (shown in 2 panels: A and B) shows the construction of six-finger proteins containing domains recognizing 5'-ANN-3' DNA sequences and ELISA analysis. A: The six-finger proteins pAart, pE2X, pE3Y and pE3Z were constructed using the Sp1C framework. Amino acid residues in position-1 to 6 of the α-recognition helix are given for each finger that was utilized. B: Proteins were expressed in E. coli as MBP fusion proteins. Specificity of binding was analyzed by measurement of the binding activity from crude lysates to immobilized biotinylated oligonucleotides (E2X, 5'-ACC GGA GAA ACC AGG GGA-3' (SEQ ID NO. 72); E3Y, 5'-ATC GAG GCA AGA GCC ACC-' (SEQ ID NO: 73); E3Z,5'-GCC GCA GCA GCC ACC AAT-3' (SEQ ID NO: 74);Aart, 5'-ATG-TAG-AGA-AAA-ACC-AGG-3' (SEQ ID NO: 75)). Assays were performed in duplicates, bars representing the standard deviation. Black bars: pE2X; striped bars: pE3Y; Gray bars: pE3Y; white bars: pAart.

The 6-finger protein pE2X binding to the target site 5'-ACC GGA GAA ACC AGG GGA-3' (SEQ ID NO: 101) in position-168 to −151 in the 5' untranslated region (UTR) of the erbB-2 gene was constructed (FIG. 4a). In addition, two proteins binding in the 5' UTR of the erbB-3 gene were generated. The protein pE3Y bound to the target site 5'-ATC GAG GCA AGA GCC ACC-3' (SEQ ID NO: 102) in position-94 to 111 of the 5' UTR, pE3Z in position-79 to 61 recognizing 5'-GCC GCA GCA GCC ACC AAT-3' (SEQ ID NO: 103) (FIG. 4a). The coding sequence for the four 6-finger proteins were then cloned into the bacterial expression vector pMal. Crude extracts containing the zinc finger-MBP fusion protein were tested for DNA binding in ELISA (FIG. 4b). All four proteins show exquisite binding specificity to their target DNA with no cross-reactivity to the other target sites tested. The affinities were determined in gel mobility shift assays with purified proteins. The protein Aart bound its DNA target site with an affinity of 7.5 pM, pE2X with an affinity of 15 nM, pE3Y of 8 nM and pE3Z of 2 nM, which is in the range of affinities we have observed for most 6-finger proteins analyzed so far.

Figure 5A:
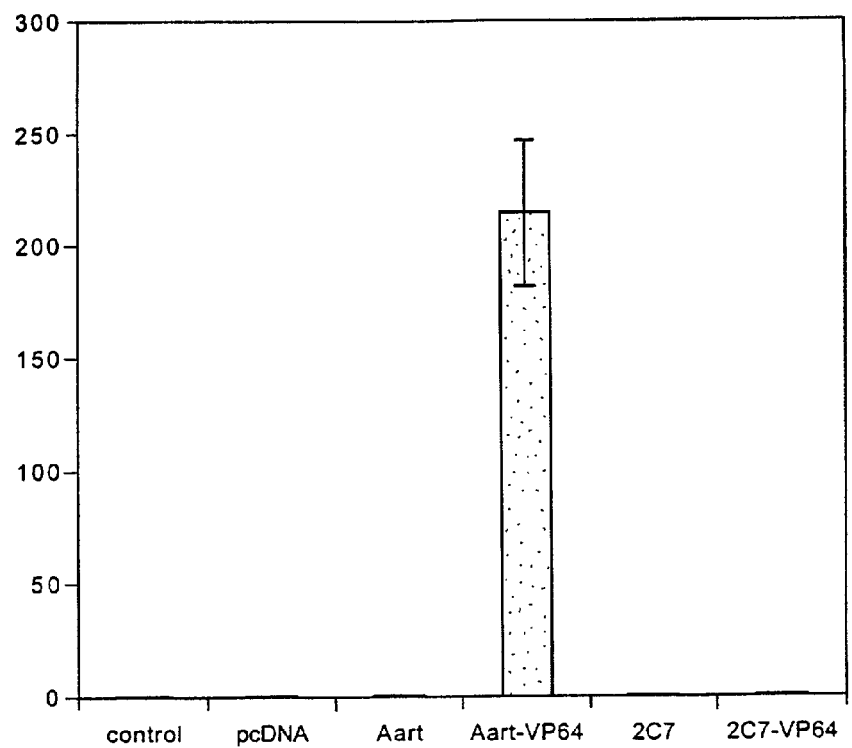
FIG. 5 (shown in 2 panels: A and B) shows luciferase reporter assay results. HeLa cells were cotransfected with the indicated zinc finger expression plasmid (pcDNA as control) and a reporter plasmid containing a luciferase gene under the control of a minimal promoter with TATA-box and zinc finger-binding sites (A: 5×Aart binding site; B: 6×2C7 binding sites). Luciferase activity in cell extracts was measured 48 h after transfection. Each bar represents the mean value (+/−standard deviation) of duplicate measurements. Y-axis: light units divided by $10^3$. X-axis: constructs coding for zinc finger proteins transfected; control: reporter alone; -: pcDNA.
Figure 5B:
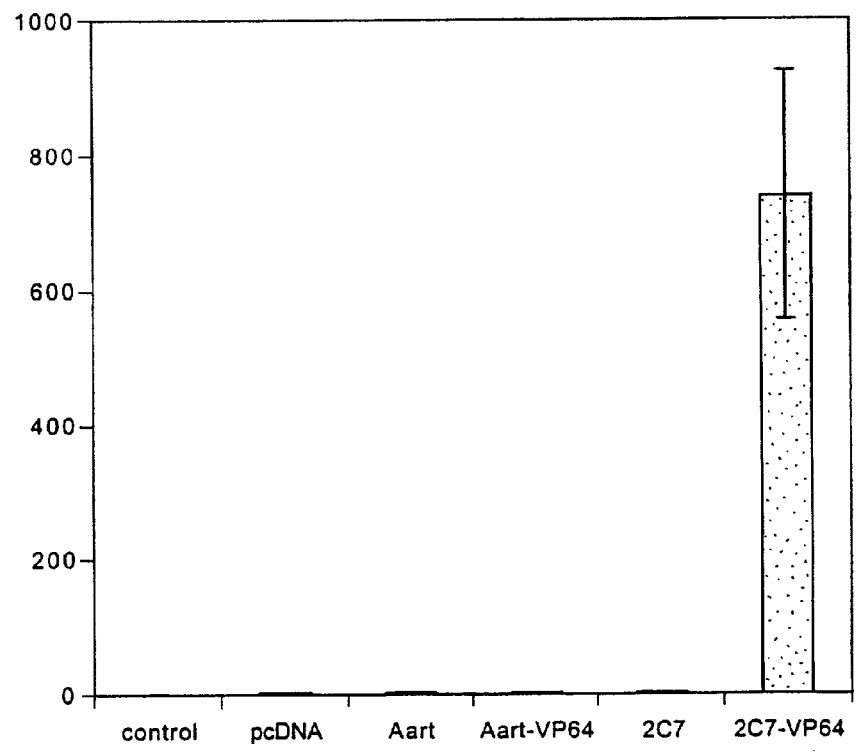

To evaluate the potential for specific gene regulation, the protein-coding sequence for Aart was cloned into the vector pcDNA and fused to the VP64 activation domain, a tetrameric repeat of the minimal activation domain derived from the herpes simplex virus protein VP16 [Seipel et al., (1992) *EMBO J.* 11(13), 4961–4968; Beerli et al., (1998) *Proc Natl Acad Sci USA* 95(25), 14628–14633]. HeLa cells were transiently co-transfected with the effector constructs coding either only for the zinc finger protein or as fusion with the VP64 domain, and a luciferase reporter plasmid under the control of a minimal promoter containing the zinc finger-binding site and a TATA-box. The Aart-binding site was present in five copies while a promoter used as control contained six 2C7-binding sites. The expression of luciferase was up-regulated 2000-fold by the pAart-VP64 fusion protein in comparison to the control containing no activation domain (FIG. 5a). Activation was specific since no regulation of the reporter containing 6×2C7-binding sites was observed (FIG. 5b). As additional control for specificity the 6-finger protein p2C7 [Wu et al., (1995) *PNAS* 92, 344–348] was also tested, which only activated luciferase expression when the promoter contained 6×2C7-binding sites (FIG. 5b), but not when the promoter contained the 5×Aart-binding (FIG. 5a). The 3-finger proteins of each half site of pAart fused to VP64 were not capable of activating luciferase expression which is consistent with previous results [Beerli et al., (2000) *Proc Natl Acad Sci USA* 97(4), 1495–1500; Beerli et al., (2000) *J. Biol. Chem.* 275(42), 32617–32627].

Figure 6A:
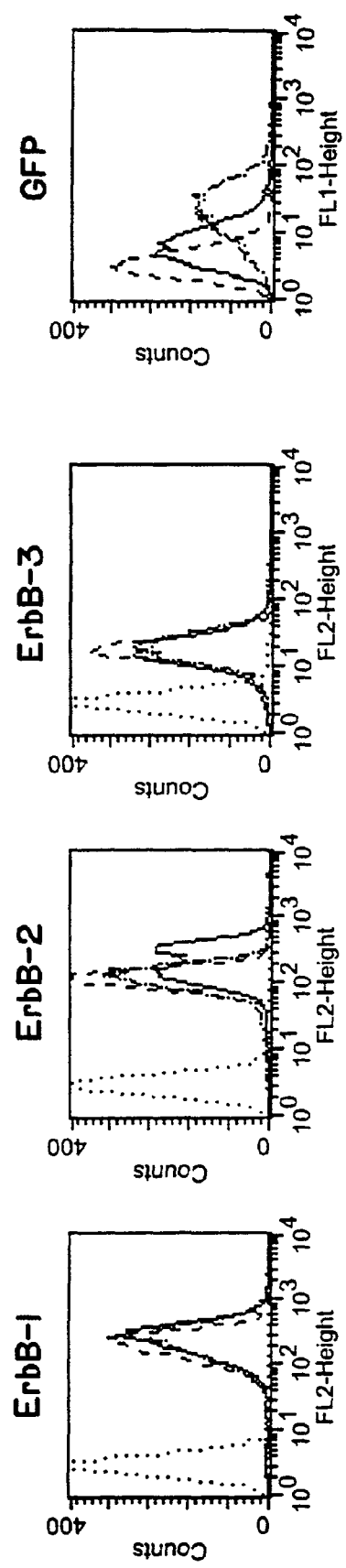
FIG. 6 (shown in 2 panels: A and B) shows retrovirus-mediated gene targeting. A431 cells were infected with retrovirus encoding for pE2X (A) or pE3Y (B) fused to either the activation domain VP64 or repression domain KRAB, respectively. Three days later, intact cells were stained with the ErbB-1-specific mab EGFR-1, the ErbB-2-specific mAb FSP77, or the ErbB-3 specific mAb SGP1 in combination with phycoerythrin-labeled secondary antibody. Dotted lines: control staining (primary antibody omitted); dashed lines: specific staining of mock-infected cells; dotted/dashed lines: cells expressing zinc finger protein-VP64 fusions; solid lines: cells expressing zinc finger protein-KRAB fusions.
Figure 6B:
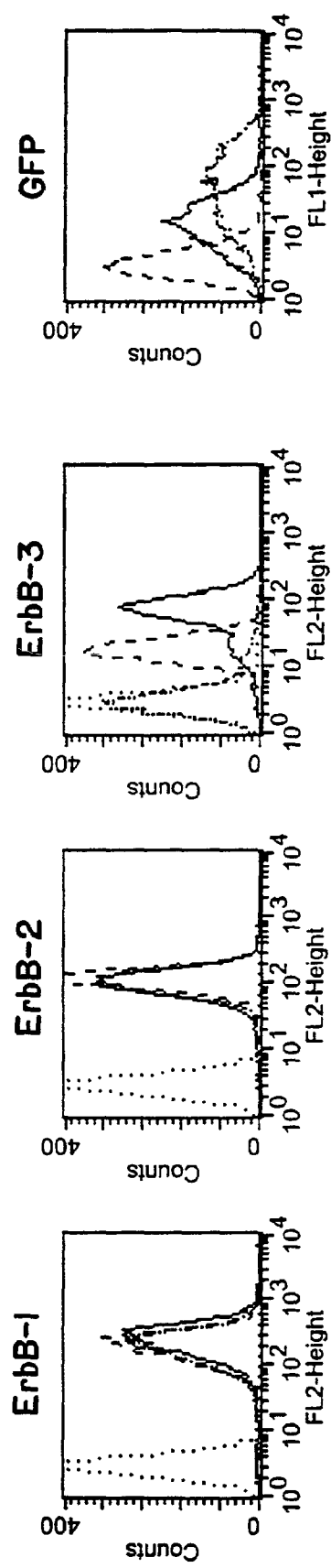

To investigate the ability of the 6-finger proteins pE2X, pE3Y and pE3Z to transcriptionally regulate the endogenous erbB-2 and erbB-3 genes, respectively, the coding sequences were subcloned into the retroviral vector pMX-IRES-GFP and fused to the VP64 activation or the KRAB repression domain of Kox-1[Margolin et al., (1994) *Proc. Natl. Acad. Sci. USA* 91, 4509–4513; Beerli et al., (1998) *Proc Natl Acad Sci USA* 95(25), 14628–14633]. Retrovirus was used to infect the human carcinoma cell line A431. Three days after infection cells were subjected to flow cytometry to analyze expression levels of ErbB-2 and ErbB-3 (FIG. 6). The infection efficiency was determined by measurement of GFP expression. All cell pools, with the exception of pE2X-VP64, were infected to more than 80%. To determine the expression levels of ErbB-2 and ErbB-3, cells were stained with specific antibodies, or a control antibody specific for ErbB-1. The fusion protein pE2X-VP64 was capable to up-regulate ErbB-2 expression but only in 50% of the cells which is likely to be due to the low infection efficiency. pE3Y showed specific up- and down-regulation when fused to VP64 or KRAB, respectively, which was as efficient as the previously reported pE3. The pE3Z fusion proteins did not alter gene expression of erbB-3, even though pE3Z had the highest affinity of the 3 generated proteins. The zinc finger domains described herein specifically recognizing 5'-ANN-3' DNA sequences greatly contribute to the number of 6-finger proteins that can now be constructed and DNA sequences that can be targeted by zinc finger-based transcription factors.

EXAMPLE 1

Construction of Zinc Finger Library and Selection Via Phage Display

Construction of the zinc finger library was based on the earlier described C7 protein ([Wu et al., (1995) *PNAS* 92, 344–348]; FIG. 1a, upper panel). Finger 3 recognizing the 5'-GCG-3' subsite was replaced by a domain binding to a 5'-GAT-3' subsite [Segal et al., (1999) *Proc Natl Acad Sci USA* 96(6), 2758–2763] via a overlap PCR strategy using a primer coding for finger 3 (5'-GAGGAAGTTTGCCAC-CAGTGGCAACCTG GTGAGGCATACCAAAATC-3') (SEQ ID NO: 104) and a pMal-specific primer (5'-GTAAAACGACGGCCAGTGCCAAGC-3') (SEQ ID NO: 105). Randomization the zinc finger library by PCR overlap extension was essentially as described [Wu et al., (1995) *PNAS* 92, 344–348; Segal et al., (1999) *Proc Natl Acad Sci USA* 96(6), 2758–2763]. The library was ligated into the phagemid vector pComb3H [Rader et al., (1997) *Curr. Opin. Biotechnol.* 8(4), 503–508]. Growth and precipitation of phage were performed as previously described [Barbas et al., (1991) *Methods: Companion Methods Enzymol.* 2(2), 119–124; Barbas et al., (1991) *Proc. Natl. Acad. Sci. USA* 88, 7978–7982; Segal et al., (1999) *Proc Natl Acad Sci USA* 96(6), 2758–2763]. Binding reactions were performed in a volume of 500 µl zinc buffer A (ZBA: 10 mM Tris, pH 7.5/90 mM KCl/1 mM $MgCl_2$/90 µM $ZnCl_2$)/0.2% BSA/5 mM DTT/1% Blotto (Biorad)/20 µg double-stranded, sheared herring sperm DNA containing 100 µl precipitated phage ($10^{13}$ colony-forming units). Phage were allowed to bind to non-biotinylated competitor oligonucleotides for 1 hr at 4° C. before the biotinylated target oligonucleotide was added. Binding continued overnight at 4° C. After incubation with 50 µl streptavidin coated magnetic beads (Dynal; blocked with 5% Blotto in ZBA) for 1 hr, beads were washed ten times with 500 µl ZBA/2% Tween 20/5 mM DTT, and once with buffer containing no Tween. Elution of bound phage was performed by incubation in 25 µl trypsin (10 mg/ml) in TBS (Tris-buffered saline) for 30 min at room temperature. Hairpin competitor oligonucleotides had the sequence 5'-GGCCGCN'N'N'ATC GAGTTTTCTCGATNNNGCG-GCC-3' (SEQ ID NO: 106) (target oligonucleotides were biotinylated), where NNN represents the finger-2 subsite oligonucleotides, N'N'N' its complementary bases. Target oligonucleotides were usually added at 72 nM in the first three rounds of selection, then decreased to 36 nM and 18 nM in the sixth and last round. As competitor a 5'-TGG-3' finger-2 subsite oligonucleotide was used to compete with the parental clone. An equimolar mixture of 15 finger-2 5'-ANN-3' subsites, except for the target site, respectively, and competitor mixtures of each finger-2 subsites of the type 5'-CNN-3',5'-GNN-3', and 5'-TNN-3' were added in increasing amounts with each successive round of selection. Usually no specific 5'-ANN-3' competitor mix was added in the first round.

Multitarget Specificity Assay and Gel Mobility Shift Analysis—The zinc finger-coding sequence was subcloned from pComb3H into a modified bacterial expression vector pMal-c2 (New England Biolabs). After transformation into XL1-Blue (Stratagene) the zinc finger-maltose-binding protein (MBP) fusions were expressed after addition of 1 nM isopropyl β-D-thiogalactoside (IPTG). Freeze/thaw extracts of these bacterial cultures were applied in 1:2 dilutions to 96-well plates coated with streptavidin (Pierce), and were tested for DNA-binding specificity against each of the sixteen 5'-GAT ANN GCG-3' target sites, respectively. ELISA (enzyme-linked immunosorbant assay) was performed essentially as described [Segal et al., (1999) *Proc Natl Acad Sci USA* 96(6), 2758–2763; Dreier et al., (2000) *J. Mol. Biol* 303, 489–502]. After incubation with a mouse anti-MBP (maltose-binding protein) antibody (Sigma, 1:1000), a goat anti-mouse antibody coupled with alkaline phosphatase (Sigma, 1:1000) was applied. Detection followed by addition of alkaline phosphatase substrate (Sigma), and the OD405 was determined with SOFT-MAX2.35 (Molecular Devices).

Gelshift analysis was performed with purified protein (Protein Fusion and Purification System, New England Biolabs) essentially as described.

EXAMPLE 2

Site-Directed Mutagenesis of Finger 2

Finger-2 mutants were constructed by PCR as described [Segal et al., (1999) *Proc Natl Acad Sci USA* 96(6), 2758–2763; Dreier et al., (2000) *J. Mol. Biol.* 303, 489–502]. As PCR template the library clone containing 5'-TGG-3' finger 2 and 5'-GAT-3' finger 3 was used. PCR products containing a mutagenized finger 2 and 5'-GAT-3' finger 3 were subcloned via NsiI and SpeI restriction sites in frame with finger 1 of C7 into a modified pMal-c2 vector (New England Biolabs).

Construction of Polydactyl Zinc Finger Proteins—Three-finger proteins were constructed by finger-2 stitchery using the SP1C framework as described [Beerli et al., (1998) *Proc Natl Acad Sci USA* 95(25), 14628–14633]. The proteins generated in this work contained helices recognizing 5'-GNN-3' DNA sequences [Segal et al., (1999) *Proc Natl Acad Sci USA* 96(6), 2758–2763], as well as 5'-ANN-3' and 5'-TAG-3' helic described here. Six finger proteins were assembled via compatible XmaI and BsrFIes restriction sites. Analysis of DNA-binding properties were performed from IPTG-induced freeze/thaw bacterial extracts. For the analysis of capability of these proteins to regulate gene expression they were fused to the activation domain VP64 or repression domain KRAB of Kox-1 as described earlier ([Beerli et al., (1998) *Proc Natl Acad Sci USA* 95(25), 14628–14633; Beerli et al., (2000) *Proc Natl Acad Sci USA* 97(4), 1495–1500; Beerli et al., (2000) *J. Biol. Chem.* 275(42), 32617–32627]; VP64: tetrameric repeat of herpes simplex virus' VP16 minimal activation domain) and subcloned into pcDNA3 or the retroviral pMX-IRES-GFP vector ([Liu et al., (1997) *Proc. Natl. Acad. Sci. USA* 94, 10669–10674]; IRES, internal ribosome-entry site; GFP, green fluorescent protein).

EXAMPLE 3

General Methods

Transfection and Luciferase Assays

HeLa cells were used at a confluency of 40–60%. Cells were transfected with 160 ng reporter plasmid (pGL3-promoter constructs) and 40 ng of effector plasmid (zinc finger-effector domain fusions in pcDNA3) in 24 well plates. Cell extracts were prepared 48 hrs after transfection and measured with luciferase assay reagent (Promega) in a MicroLumat LB96P luminometer (EG & Berthold, Gaithersburg, Md.).

Retroviral Gene Targeting and Flow Cytometric Analysis

These assays were performed as described [Beerli et al., (2000) *Proc Natl Acad Sci USA* 97(4), 1495–1500; Beerli et al., (2000) *J. Biol. Chem.* 275(42), 32617–32627]. As primary antibody an ErbB-1-specific mAb EGFR (Santa Cruz), ErbB-2-specific mAb FSP77 (gift from Nancy E. Hynes; Harwerth et al., 1992) and an ErbB-3-specific mAb SGP1 (Oncogene Research Products) were used. Fluorescently labeled donkey F(ab')2 anti-mouse IgG was used as secondary antibody (Jackson Immuno-Research).

Computer Modeling

Computer models were generated using InsightII (Molecular Simulations, Inc.). Models were based on the coordinates of the co-crystal structures of Zif268-DNA (PDB accession 1AAY) and QGSR-GCAC (SEQ ID NO: 107) (1A1H). The structures were not energy minimized and are presented only to suggest possible interactions. Hydrogen bonds were considered plausible when the distance between the heavy atoms was 3(+/− 0.3) Å and the angle formed by the heavy atoms and hydrogen was 1200 or greater. Plausible van der Waals interactions required a distance between methyl group carbon atoms of 4(+/− 0.3) Å.

---

What is claimed is:

1. An isolated polypeptide comprising from 2 to 12 zinc finger-nucleotide binding peptides at least one of which peptides contains a nucleotide binding region having the sequence of SEQ ID NO: 46.

2. The polypeptide of claim 1 containing from 2 to 6 zinc finger-nucleotide binding peptides.

3. The polypeptide of claim 1 wherein each of the peptides binds to a different target nucleotide sequence.

4. The polypeptide of claim 2 that binds to a nucleotide sequence that contains the sequence 5'-(ANN)$_n$-3', wherein each N is A, C, G, or T and where n is 2 to 6.

5. The polypeptide of claim 1 further operatively linked to one or more transcription regulating factors.

6. The polypeptide of claim 1 wherein each of the peptides contains a nucleotide binding region having the sequence of SEQ ID NO: 46.

* * * * *

SEQUENCE LISTING

```
<160> NUMBER OF SEQ ID NOS: 113

<210> SEQ ID NO 1
<211> LENGTH: 7
<212> TYPE: PRT
<213> ORGANISM: Artificial Sequence
<220> FEATURE:
<223> OTHER INFORMATION: synthesized

<400> SEQUENCE: 1

Lys Ser Ala Asp Leu Lys Arg
 1               5

<210> SEQ ID NO 2
<211> LENGTH: 7
<212> TYPE: PRT
```

```
<213> ORGANISM: Artificial Sequence
<220> FEATURE:
<223> OTHER INFORMATION: synthesized

<400> SEQUENCE: 2

Arg Ser Asp His Leu Thr Thr
1               5

<210> SEQ ID NO 3
<211> LENGTH: 7
<212> TYPE: PRT
<213> ORGANISM: Artificial Sequence
<220> FEATURE:
<223> OTHER INFORMATION: synthesized

<400> SEQUENCE: 3

Arg Ser Asp Glu Leu Lys Arg
1               5

<210> SEQ ID NO 4
<211> LENGTH: 7
<212> TYPE: PRT
<213> ORGANISM: Artificial Sequence
<220> FEATURE:
<223> OTHER INFORMATION: synthesized

<400> SEQUENCE: 4

Lys Ser Ala Asp Leu Lys Arg
1               5

<210> SEQ ID NO 5
<211> LENGTH: 7
<212> TYPE: PRT
<213> ORGANISM: Artificial Sequence
<220> FEATURE:
<223> OTHER INFORMATION: synthesized

<400> SEQUENCE: 5

Arg Ser Asp His Leu Thr Thr
1               5

<210> SEQ ID NO 6
<211> LENGTH: 7
<212> TYPE: PRT
<213> ORGANISM: Artificial Sequence
<220> FEATURE:
<223> OTHER INFORMATION: synthesized

<400> SEQUENCE: 6

Thr Ser Gly Asn Leu Val Arg
1               5

<210> SEQ ID NO 7
<211> LENGTH: 8
<212> TYPE: PRT
<213> ORGANISM: Artificial Sequence
<220> FEATURE:
<223> OTHER INFORMATION: synthesized

<400> SEQUENCE: 7

Ser Thr Asn Thr Lys Leu His Ala
1               5

<210> SEQ ID NO 8
<211> LENGTH: 8
<212> TYPE: PRT
<213> ORGANISM: Artificial Sequence
```

```
<220> FEATURE:
<223> OTHER INFORMATION: synthesized

<400> SEQUENCE: 8

Ser Ser Asp Arg Thr Leu Arg Arg
1               5

<210> SEQ ID NO 9
<211> LENGTH: 8
<212> TYPE: PRT
<213> ORGANISM: Artificial Sequence
<220> FEATURE:
<223> OTHER INFORMATION: synthesized

<400> SEQUENCE: 9

Ser Thr Lys Glu Arg Leu Lys Thr
1               5

<210> SEQ ID NO 10
<211> LENGTH: 8
<212> TYPE: PRT
<213> ORGANISM: Artificial Sequence
<220> FEATURE:
<223> OTHER INFORMATION: synthesized

<400> SEQUENCE: 10

Ser Gln Arg Ala Asn Leu Arg Ala
1               5

<210> SEQ ID NO 11
<211> LENGTH: 8
<212> TYPE: PRT
<213> ORGANISM: Artificial Sequence
<220> FEATURE:
<223> OTHER INFORMATION: synthesized

<400> SEQUENCE: 11

Ser Ser Pro Ala Asp Leu Thr Arg
1               5

<210> SEQ ID NO 12
<211> LENGTH: 8
<212> TYPE: PRT
<213> ORGANISM: Artificial Sequence
<220> FEATURE:
<223> OTHER INFORMATION: synthesized

<400> SEQUENCE: 12

Ser Ser His Ser Asp Leu Val Arg
1               5

<210> SEQ ID NO 13
<211> LENGTH: 8
<212> TYPE: PRT
<213> ORGANISM: Artificial Sequence
<220> FEATURE:
<223> OTHER INFORMATION: synthesized

<400> SEQUENCE: 13

Ser Asn Gly Gly Glu Leu Ile Arg
1               5

<210> SEQ ID NO 14
<211> LENGTH: 8
<212> TYPE: PRT
<213> ORGANISM: Artificial Sequence
<220> FEATURE:
```

```
<223> OTHER INFORMATION: synthesized

<400> SEQUENCE: 14

Ser His Gln Leu Ile Leu Leu Lys
1               5

<210> SEQ ID NO 15
<211> LENGTH: 8
<212> TYPE: PRT
<213> ORGANISM: Artificial Sequence
<220> FEATURE:
<223> OTHER INFORMATION: synthesized

<400> SEQUENCE: 15

Ser Ser Arg Met Asp Leu Lys Arg
1               5

<210> SEQ ID NO 16
<211> LENGTH: 8
<212> TYPE: PRT
<213> ORGANISM: Artificial Sequence
<220> FEATURE:
<223> OTHER INFORMATION: synthesized

<400> SEQUENCE: 16

Ser Arg Ser Asp His Leu Thr Asn
1               5

<210> SEQ ID NO 17
<211> LENGTH: 8
<212> TYPE: PRT
<213> ORGANISM: Artificial Sequence
<220> FEATURE:
<223> OTHER INFORMATION: synthesized

<400> SEQUENCE: 17

Ser Gln Leu Ala His Leu Arg Ala
1               5

<210> SEQ ID NO 18
<211> LENGTH: 8
<212> TYPE: PRT
<213> ORGANISM: Artificial Sequence
<220> FEATURE:
<223> OTHER INFORMATION: synthesized

<400> SEQUENCE: 18

Ser Gln Ala Ser Ser Leu Lys Ala
1               5

<210> SEQ ID NO 19
<211> LENGTH: 8
<212> TYPE: PRT
<213> ORGANISM: Artificial Sequence
<220> FEATURE:
<223> OTHER INFORMATION: synthesized

<400> SEQUENCE: 19

Ser Gln Lys Ser Ser Leu Ile Ala
1               5

<210> SEQ ID NO 20
<211> LENGTH: 8
<212> TYPE: PRT
<213> ORGANISM: Artificial Sequence
<220> FEATURE:
<223> OTHER INFORMATION: synthesized
```

```
<400> SEQUENCE: 20

Ser Arg Lys Asp Asn Leu Lys Asn
1               5

<210> SEQ ID NO 21
<211> LENGTH: 8
<212> TYPE: PRT
<213> ORGANISM: Artificial Sequence
<220> FEATURE:
<223> OTHER INFORMATION: synthesized

<400> SEQUENCE: 21

Ser Asp Ser Gly Asn Leu Arg Val
1               5

<210> SEQ ID NO 22
<211> LENGTH: 8
<212> TYPE: PRT
<213> ORGANISM: Artificial Sequence
<220> FEATURE:
<223> OTHER INFORMATION: synthesized

<400> SEQUENCE: 22

Ser Asp Arg Arg Asn Leu Arg Arg
1               5

<210> SEQ ID NO 23
<211> LENGTH: 8
<212> TYPE: PRT
<213> ORGANISM: Artificial Sequence
<220> FEATURE:
<223> OTHER INFORMATION: synthesized

<400> SEQUENCE: 23

Ser Asp Lys Lys Asp Leu Thr Arg
1               5

<210> SEQ ID NO 24
<211> LENGTH: 8
<212> TYPE: PRT
<213> ORGANISM: Artificial Sequence
<220> FEATURE:
<223> OTHER INFORMATION: synthesized

<400> SEQUENCE: 24

Ser Asp Ala Ser His Leu His Thr
1               5

<210> SEQ ID NO 25
<211> LENGTH: 8
<212> TYPE: PRT
<213> ORGANISM: Artificial Sequence
<220> FEATURE:
<223> OTHER INFORMATION: synthesized

<400> SEQUENCE: 25

Ser Thr Asn Thr Gly Leu Lys Asn
1               5

<210> SEQ ID NO 26
<211> LENGTH: 8
<212> TYPE: PRT
<213> ORGANISM: Artificial Sequence
<220> FEATURE:
<223> OTHER INFORMATION: synthesized
```

```
<400> SEQUENCE: 26

Ser Thr Arg Met Ser Leu Ser Thr
1               5

<210> SEQ ID NO 27
<211> LENGTH: 8
<212> TYPE: PRT
<213> ORGANISM: Artificial Sequence
<220> FEATURE:
<223> OTHER INFORMATION: synthesized

<400> SEQUENCE: 27

Ser Asn His Asp Ala Leu Arg Ala
1               5

<210> SEQ ID NO 28
<211> LENGTH: 8
<212> TYPE: PRT
<213> ORGANISM: Artificial Sequence
<220> FEATURE:
<223> OTHER INFORMATION: synthesized

<400> SEQUENCE: 28

Ser Arg Arg Ser Ala Cys Arg Arg
1               5

<210> SEQ ID NO 29
<211> LENGTH: 8
<212> TYPE: PRT
<213> ORGANISM: Artificial Sequence
<220> FEATURE:
<223> OTHER INFORMATION: synthesized

<400> SEQUENCE: 29

Ser Arg Arg Ser Ser Cys Arg Lys
1               5

<210> SEQ ID NO 30
<211> LENGTH: 8
<212> TYPE: PRT
<213> ORGANISM: Artificial Sequence
<220> FEATURE:
<223> OTHER INFORMATION: synthesized

<400> SEQUENCE: 30

Ser Arg Ser Asp Thr Leu Ser Asn
1               5

<210> SEQ ID NO 31
<211> LENGTH: 8
<212> TYPE: PRT
<213> ORGANISM: Artificial Sequence
<220> FEATURE:
<223> OTHER INFORMATION: synthesized

<400> SEQUENCE: 31

Ser Arg Met Gly Asn Leu Ile Arg
1               5

<210> SEQ ID NO 32
<211> LENGTH: 8
<212> TYPE: PRT
<213> ORGANISM: Artificial Sequence
<220> FEATURE:
<223> OTHER INFORMATION: synthesized

<400> SEQUENCE: 32
```

```
Ser Arg Thr Asp Thr Leu Arg Asp
1               5
```

<210> SEQ ID NO 33
<211> LENGTH: 8
<212> TYPE: PRT
<213> ORGANISM: Artificial Sequence
<220> FEATURE:
<223> OTHER INFORMATION: synthesized

<400> SEQUENCE: 33

```
Ser Arg Ala His Asp Leu Val Arg
1               5
```

<210> SEQ ID NO 34
<211> LENGTH: 8
<212> TYPE: PRT
<213> ORGANISM: Artificial Sequence
<220> FEATURE:
<223> OTHER INFORMATION: synthesized

<400> SEQUENCE: 34

```
Ser Arg Ser Asp His Leu Ala Glu
1               5
```

<210> SEQ ID NO 35
<211> LENGTH: 8
<212> TYPE: PRT
<213> ORGANISM: Artificial Sequence
<220> FEATURE:
<223> OTHER INFORMATION: synthesized

<400> SEQUENCE: 35

```
Ser Arg Arg Asp Ala Leu Asn Val
1               5
```

<210> SEQ ID NO 36
<211> LENGTH: 8
<212> TYPE: PRT
<213> ORGANISM: Artificial Sequence
<220> FEATURE:
<223> OTHER INFORMATION: synthesized

<400> SEQUENCE: 36

```
Ser Thr Thr Gly Asn Leu Thr Val
1               5
```

<210> SEQ ID NO 37
<211> LENGTH: 8
<212> TYPE: PRT
<213> ORGANISM: Artificial Sequence
<220> FEATURE:
<223> OTHER INFORMATION: synthesized

<400> SEQUENCE: 37

```
Ser Thr Ser Gly Asn Leu Leu Val
1               5
```

<210> SEQ ID NO 38
<211> LENGTH: 8
<212> TYPE: PRT
<213> ORGANISM: Artificial Sequence
<220> FEATURE:
<223> OTHER INFORMATION: synthesized

<400> SEQUENCE: 38

Ser Thr Leu Thr Ile Leu Lys Asn
1               5

<210> SEQ ID NO 39
<211> LENGTH: 8
<212> TYPE: PRT
<213> ORGANISM: Artificial Sequence
<220> FEATURE:
<223> OTHER INFORMATION: synthesized

<400> SEQUENCE: 39

Ser Arg Met Ser Thr Leu Arg His
1               5

<210> SEQ ID NO 40
<211> LENGTH: 8
<212> TYPE: PRT
<213> ORGANISM: Artificial Sequence
<220> FEATURE:
<223> OTHER INFORMATION: synthesized

<400> SEQUENCE: 40

Ser Thr Arg Thr Asp Leu Leu Arg
1               5

<210> SEQ ID NO 41
<211> LENGTH: 8
<212> TYPE: PRT
<213> ORGANISM: Artificial Sequence
<220> FEATURE:
<223> OTHER INFORMATION: synthesized

<400> SEQUENCE: 41

Ser Thr Lys Thr Asp Leu Lys Arg
1               5

<210> SEQ ID NO 42
<211> LENGTH: 8
<212> TYPE: PRT
<213> ORGANISM: Artificial Sequence
<220> FEATURE:
<223> OTHER INFORMATION: synthesized

<400> SEQUENCE: 42

Ser Thr His Ile Asp Leu Ile Arg
1               5

<210> SEQ ID NO 43
<211> LENGTH: 8
<212> TYPE: PRT
<213> ORGANISM: Artificial Sequence
<220> FEATURE:
<223> OTHER INFORMATION: synthesized

<400> SEQUENCE: 43

Ser His Arg Thr Thr Leu Leu Asn
1               5

<210> SEQ ID NO 44
<211> LENGTH: 8
<212> TYPE: PRT
<213> ORGANISM: Artificial Sequence
<220> FEATURE:
<223> OTHER INFORMATION: synthesized

<400> SEQUENCE: 44

Ser Thr Ser His Gly Leu Thr Thr

-continued

```
<210> SEQ ID NO 45
<211> LENGTH: 8
<212> TYPE: PRT
<213> ORGANISM: Artificial Sequence
<220> FEATURE:
<223> OTHER INFORMATION: synthesized

<400> SEQUENCE: 45

Ser His Lys Asn Ala Leu Gln Asn
 1               5

<210> SEQ ID NO 46
<211> LENGTH: 7
<212> TYPE: PRT
<213> ORGANISM: Artificial Sequence
<220> FEATURE:
<223> OTHER INFORMATION: synthesized

<400> SEQUENCE: 46

Gln Arg Ala Asn Leu Arg Ala
 1               5

<210> SEQ ID NO 47
<211> LENGTH: 7
<212> TYPE: PRT
<213> ORGANISM: Artificial Sequence
<220> FEATURE:
<223> OTHER INFORMATION: synthesized

<400> SEQUENCE: 47

Asp Ser Gly Asn Leu Arg Val
 1               5

<210> SEQ ID NO 48
<211> LENGTH: 7
<212> TYPE: PRT
<213> ORGANISM: Artificial Sequence
<220> FEATURE:
<223> OTHER INFORMATION: synthesized

<400> SEQUENCE: 48

Arg Ser Asp Thr Leu Ser Asn
 1               5

<210> SEQ ID NO 49
<211> LENGTH: 7
<212> TYPE: PRT
<213> ORGANISM: Artificial Sequence
<220> FEATURE:
<223> OTHER INFORMATION: synthesized

<400> SEQUENCE: 49

Thr Thr Gly Asn Leu Thr Val
 1               5

<210> SEQ ID NO 50
<211> LENGTH: 7
<212> TYPE: PRT
<213> ORGANISM: Artificial Sequence
<220> FEATURE:
<223> OTHER INFORMATION: synthesized

<400> SEQUENCE: 50

Ser Pro Ala Asp Leu Thr Arg
 1               5
```

<210> SEQ ID NO 51
<211> LENGTH: 7
<212> TYPE: PRT
<213> ORGANISM: Artificial Sequence
<220> FEATURE:
<223> OTHER INFORMATION: synthesized

<400> SEQUENCE: 51

Asp Lys Lys Asp Leu Thr Arg
1               5

<210> SEQ ID NO 52
<211> LENGTH: 7
<212> TYPE: PRT
<213> ORGANISM: Artificial Sequence
<220> FEATURE:
<223> OTHER INFORMATION: synthesized

<400> SEQUENCE: 52

Arg Thr Asp Thr Leu Arg Asp
1               5

<210> SEQ ID NO 53
<211> LENGTH: 7
<212> TYPE: PRT
<213> ORGANISM: Artificial Sequence
<220> FEATURE:
<223> OTHER INFORMATION: synthesized

<400> SEQUENCE: 53

Thr His Leu Asp Leu Ile Arg
1               5

<210> SEQ ID NO 54
<211> LENGTH: 7
<212> TYPE: PRT
<213> ORGANISM: Artificial Sequence
<220> FEATURE:
<223> OTHER INFORMATION: synthesized

<400> SEQUENCE: 54

Gln Leu Ala His Leu Arg Ala
1               5

<210> SEQ ID NO 55
<211> LENGTH: 7
<212> TYPE: PRT
<213> ORGANISM: Artificial Sequence
<220> FEATURE:
<223> OTHER INFORMATION: synthesized

<400> SEQUENCE: 55

Arg Ser Asp His Leu Ala Glu
1               5

<210> SEQ ID NO 56
<211> LENGTH: 7
<212> TYPE: PRT
<213> ORGANISM: Artificial Sequence
<220> FEATURE:
<223> OTHER INFORMATION: synthesized

<400> SEQUENCE: 56

His Arg Thr Thr Leu Leu Asn
1               5

```
<210> SEQ ID NO 57
<211> LENGTH: 7
<212> TYPE: PRT
<213> ORGANISM: Artificial Sequence
<220> FEATURE:
<223> OTHER INFORMATION: synthesized

<400> SEQUENCE: 57

Gln Lys Ser Ser Leu Ile Ala
 1               5

<210> SEQ ID NO 58
<211> LENGTH: 7
<212> TYPE: PRT
<213> ORGANISM: Artificial Sequence
<220> FEATURE:
<223> OTHER INFORMATION: synthesized

<400> SEQUENCE: 58

Arg Arg Asp Ala Leu Asn Val
 1               5

<210> SEQ ID NO 59
<211> LENGTH: 7
<212> TYPE: PRT
<213> ORGANISM: Artificial Sequence
<220> FEATURE:
<223> OTHER INFORMATION: synthesized

<400> SEQUENCE: 59

His Lys Asn Ala Leu Gln Asn
 1               5

<210> SEQ ID NO 60
<211> LENGTH: 7
<212> TYPE: PRT
<213> ORGANISM: Artificial Sequence
<220> FEATURE:
<223> OTHER INFORMATION: synthesized

<400> SEQUENCE: 60

Arg Ser Asp Asn Leu Ser Asn
 1               5

<210> SEQ ID NO 61
<211> LENGTH: 7
<212> TYPE: PRT
<213> ORGANISM: Artificial Sequence
<220> FEATURE:
<223> OTHER INFORMATION: synthesized

<400> SEQUENCE: 61

Arg Lys Asp Asn Leu Lys Asn
 1               5

<210> SEQ ID NO 62
<211> LENGTH: 7
<212> TYPE: PRT
<213> ORGANISM: Artificial Sequence
<220> FEATURE:
<223> OTHER INFORMATION: synthesized

<400> SEQUENCE: 62

Thr Ser Gly Asn Leu Leu Val
 1               5
```

```
<210> SEQ ID NO 63
<211> LENGTH: 7
<212> TYPE: PRT
<213> ORGANISM: Artificial Sequence
<220> FEATURE:
<223> OTHER INFORMATION: synthesized

<400> SEQUENCE: 63

Arg Ser Asp His Leu Thr Asn
 1               5

<210> SEQ ID NO 64
<211> LENGTH: 7
<212> TYPE: PRT
<213> ORGANISM: Artificial Sequence
<220> FEATURE:
<223> OTHER INFORMATION: synthesized

<400> SEQUENCE: 64

His Arg Thr Thr Leu Thr Asn
 1               5

<210> SEQ ID NO 65
<211> LENGTH: 7
<212> TYPE: PRT
<213> ORGANISM: Artificial Sequence
<220> FEATURE:
<223> OTHER INFORMATION: synthesized

<400> SEQUENCE: 65

Ser His Ser Asp Leu Val Arg
 1               5

<210> SEQ ID NO 66
<211> LENGTH: 7
<212> TYPE: PRT
<213> ORGANISM: Artificial Sequence
<220> FEATURE:
<223> OTHER INFORMATION: synthesized

<400> SEQUENCE: 66

Asn Gly Gly Glu Leu Ile Arg
 1               5

<210> SEQ ID NO 67
<211> LENGTH: 7
<212> TYPE: PRT
<213> ORGANISM: Artificial Sequence
<220> FEATURE:
<223> OTHER INFORMATION: synthesized

<400> SEQUENCE: 67

Ser Thr Lys Asp Leu Lys Arg
 1               5

<210> SEQ ID NO 68
<211> LENGTH: 7
<212> TYPE: PRT
<213> ORGANISM: Artificial Sequence
<220> FEATURE:
<223> OTHER INFORMATION: synthesized

<400> SEQUENCE: 68

Arg Arg Asp Glu Leu Asn Val
 1               5

<210> SEQ ID NO 69
```

```
<211> LENGTH: 7
<212> TYPE: PRT
<213> ORGANISM: Artificial Sequence
<220> FEATURE:
<223> OTHER INFORMATION: synthesized

<400> SEQUENCE: 69

Gln Ala Ser Ser Leu Lys Ala
 1               5

<210> SEQ ID NO 70
<211> LENGTH: 7
<212> TYPE: PRT
<213> ORGANISM: Artificial Sequence
<220> FEATURE:
<223> OTHER INFORMATION: synthesized

<400> SEQUENCE: 70

Thr Ser His Gly Leu Thr Thr
 1               5

<210> SEQ ID NO 71
<211> LENGTH: 7
<212> TYPE: PRT
<213> ORGANISM: Artificial Sequence
<220> FEATURE:
<223> OTHER INFORMATION: synthesized

<400> SEQUENCE: 71

Arg Glu Asp Asn Leu His Thr
 1               5

<210> SEQ ID NO 72
<211> LENGTH: 18
<212> TYPE: DNA
<213> ORGANISM: Artificial Sequence
<220> FEATURE:
<223> OTHER INFORMATION: synthesized

<400> SEQUENCE: 72
accggagaaa ccagggga                                              18

<210> SEQ ID NO 73
<211> LENGTH: 18
<212> TYPE: DNA
<213> ORGANISM: Artificial Sequence
<220> FEATURE:
<223> OTHER INFORMATION: synthesized

<400> SEQUENCE: 73
atcgaggcaa gagccacc                                              18

<210> SEQ ID NO 74
<211> LENGTH: 18
<212> TYPE: DNA
<213> ORGANISM: Artificial Sequence
<220> FEATURE:
<223> OTHER INFORMATION: synthesized

<400> SEQUENCE: 74
gccgcagcag ccaccaat                                              18

<210> SEQ ID NO 75
<211> LENGTH: 18
<212> TYPE: DNA
<213> ORGANISM: Artificial Sequence
<220> FEATURE:
```

<223> OTHER INFORMATION: synthesized

<400> SEQUENCE: 75
atgtagagaa aaaccagg    18

<210> SEQ ID NO 76
<211> LENGTH: 9
<212> TYPE: DNA
<213> ORGANISM: Artificial Sequence
<220> FEATURE:
<223> OTHER INFORMATION: synthesized

<400> SEQUENCE: 76 gcgtgggcg    9

<210> SEQ ID NO 77
<211> LENGTH: 7
<212> TYPE: PRT
<213> ORGANISM: Artificial Sequence
<220> FEATURE:
<223> OTHER INFORMATION: synthesized

<400> SEQUENCE: 77

Ser Pro Ala Asp Leu Thr Asn
 1               5

<210> SEQ ID NO 78
<211> LENGTH: 7
<212> TYPE: PRT
<213> ORGANISM: Artificial Sequence
<220> FEATURE:
<223> OTHER INFORMATION: synthesized

<400> SEQUENCE: 78

His Ile Ser Asn Phe Cys Arg
 1               5

<210> SEQ ID NO 79
<211> LENGTH: 7
<212> TYPE: PRT
<213> ORGANISM: Artificial Sequence
<220> FEATURE:
<223> OTHER INFORMATION: synthesized

<400> SEQUENCE: 79

Arg Ser Asp His Leu Thr Thr
 1               5

<210> SEQ ID NO 80
<211> LENGTH: 7
<212> TYPE: PRT
<213> ORGANISM: Artificial Sequence
<220> FEATURE:
<223> OTHER INFORMATION: synthesized

<400> SEQUENCE: 80

Asp Ala Ser His Leu His Thr
 1               5

<210> SEQ ID NO 81
<211> LENGTH: 7
<212> TYPE: PRT
<213> ORGANISM: Artificial Sequence
<220> FEATURE:
<223> OTHER INFORMATION: synthesized

<400> SEQUENCE: 81

Arg Arg Ser Ala Cys Arg Arg
1               5

<210> SEQ ID NO 82
<211> LENGTH: 7
<212> TYPE: PRT
<213> ORGANISM: Artificial Sequence
<220> FEATURE:
<223> OTHER INFORMATION: synthesized

<400> SEQUENCE: 82

Glu Arg Ser Lys Leu Ala Arg
1               5

<210> SEQ ID NO 83
<211> LENGTH: 7
<212> TYPE: PRT
<213> ORGANISM: Artificial Sequence
<220> FEATURE:
<223> OTHER INFORMATION: synthesized

<400> SEQUENCE: 83

Asp Pro Gly His Leu Val Arg
1               5

<210> SEQ ID NO 84
<211> LENGTH: 7
<212> TYPE: PRT
<213> ORGANISM: Artificial Sequence
<220> FEATURE:
<223> OTHER INFORMATION: synthesized

<400> SEQUENCE: 84

Asp Pro Gly Ala Leu Val Arg
1               5

<210> SEQ ID NO 85
<211> LENGTH: 7
<212> TYPE: PRT
<213> ORGANISM: Artificial Sequence
<220> FEATURE:
<223> OTHER INFORMATION: synthesized

<400> SEQUENCE: 85

Glu Arg Ser Lys Leu Arg Ala
1               5

<210> SEQ ID NO 86
<211> LENGTH: 7
<212> TYPE: PRT
<213> ORGANISM: Artificial Sequence
<220> FEATURE:
<223> OTHER INFORMATION: synthesized

<400> SEQUENCE: 86

Asp Pro Gly His Leu Arg Val
1               5

<210> SEQ ID NO 87
<211> LENGTH: 7
<212> TYPE: PRT
<213> ORGANISM: Artificial Sequence
<220> FEATURE:
<223> OTHER INFORMATION: synthesized

<400> SEQUENCE: 87

Asp Pro Gly Ala Leu Arg Val
1               5

<210> SEQ ID NO 88
<211> LENGTH: 7
<212> TYPE: PRT
<213> ORGANISM: Artificial Sequence
<220> FEATURE:
<223> OTHER INFORMATION: synthesized

<400> SEQUENCE: 88

Asp Pro Gly Ser Leu Arg Val
1               5

<210> SEQ ID NO 89
<211> LENGTH: 7
<212> TYPE: PRT
<213> ORGANISM: Artificial Sequence
<220> FEATURE:
<223> OTHER INFORMATION: synthesized

<400> SEQUENCE: 89

Val Lys Asp Tyr Leu Thr Lys
1               5

<210> SEQ ID NO 90
<211> LENGTH: 7
<212> TYPE: PRT
<213> ORGANISM: Artificial Sequence
<220> FEATURE:
<223> OTHER INFORMATION: synthesized

<400> SEQUENCE: 90

Lys Asn Trp Lys Leu Gln Ala
1               5

<210> SEQ ID NO 91
<211> LENGTH: 7
<212> TYPE: PRT
<213> ORGANISM: Artificial Sequence
<220> FEATURE:
<223> OTHER INFORMATION: synthesized

<400> SEQUENCE: 91

Ala Gln Tyr Met Leu Val Val
1               5

<210> SEQ ID NO 92
<211> LENGTH: 7
<212> TYPE: PRT
<213> ORGANISM: Artificial Sequence
<220> FEATURE:
<223> OTHER INFORMATION: synthesized

<400> SEQUENCE: 92

Gln Ser Thr Asn Leu Lys Ser
1               5

<210> SEQ ID NO 93
<211> LENGTH: 7
<212> TYPE: PRT
<213> ORGANISM: Artificial Sequence
<220> FEATURE:
<223> OTHER INFORMATION: synthesized

<400> SEQUENCE: 93

Leu Asp Phe Asn Leu Arg Thr

<210> SEQ ID NO 94
<211> LENGTH: 7
<212> TYPE: PRT
<213> ORGANISM: Artificial Sequence
<220> FEATURE:
<223> OTHER INFORMATION: synthesized

<400> SEQUENCE: 94

Arg Lys Asp Asn Met Thr Ala
1               5

<210> SEQ ID NO 95
<211> LENGTH: 7
<212> TYPE: PRT
<213> ORGANISM: Artificial Sequence
<220> FEATURE:
<223> OTHER INFORMATION: synthesized

<400> SEQUENCE: 95

Gln Ser Ser Asn Leu Ile Thr
1               5

<210> SEQ ID NO 96
<211> LENGTH: 7
<212> TYPE: PRT
<213> ORGANISM: Artificial Sequence
<220> FEATURE:
<223> OTHER INFORMATION: synthesized

<400> SEQUENCE: 96

Gln Arg Ser Ala Leu Thr Val
1               5

<210> SEQ ID NO 97
<211> LENGTH: 7
<212> TYPE: PRT
<213> ORGANISM: Artificial Sequence
<220> FEATURE:
<223> OTHER INFORMATION: synthesized

<400> SEQUENCE: 97

Gln Ser Gly Ser Leu Thr Arg
1               5

<210> SEQ ID NO 98
<211> LENGTH: 8
<212> TYPE: PRT
<213> ORGANISM: Artificial Sequence
<220> FEATURE:
<223> OTHER INFORMATION: synthesized

<400> SEQUENCE: 98

Gln Gly Ser Arg Gly Cys Ala Cys
1               5

<210> SEQ ID NO 99
<211> LENGTH: 7
<212> TYPE: PRT
<213> ORGANISM: Artificial Sequence
<220> FEATURE:
<223> OTHER INFORMATION: synthesized

<400> SEQUENCE: 99

His Ile Ser Asn Phe Cys Arg
1               5

<210> SEQ ID NO 100
<211> LENGTH: 7
<212> TYPE: PRT
<213> ORGANISM: Artificial Sequence
<220> FEATURE:
<223> OTHER INFORMATION: synthesized

<400> SEQUENCE: 100

His Lys Asn Ala Leu Gln Asn
 1               5

<210> SEQ ID NO 101
<211> LENGTH: 18
<212> TYPE: DNA
<213> ORGANISM: Artificial Sequence
<220> FEATURE:
<223> OTHER INFORMATION: synthesized

<400> SEQUENCE: 101
accggagaaa ccaggggga                                                  18

<210> SEQ ID NO 102
<211> LENGTH: 18
<212> TYPE: DNA
<213> ORGANISM: Artificial Sequence
<220> FEATURE:
<223> OTHER INFORMATION: synthesized

<400> SEQUENCE: 102
atcgaggcaa gagccacc                                                   18

<210> SEQ ID NO 103
<211> LENGTH: 18
<212> TYPE: DNA
<213> ORGANISM: Artificial Sequence
<220> FEATURE:
<223> OTHER INFORMATION: synthesized

<400> SEQUENCE: 103
gccgcagcag ccaccaat                                                   18

<210> SEQ ID NO 104
<211> LENGTH: 46
<212> TYPE: DNA
<213> ORGANISM: Artificial Sequence
<220> FEATURE:
<223> OTHER INFORMATION: synthesized

<400> SEQUENCE: 104
gaggaagttt gccaccagtg gcaacctggt gaggcatacc aaaatc                    46

<210> SEQ ID NO 105
<211> LENGTH: 24
<212> TYPE: DNA
<213> ORGANISM: Artificial Sequence
<220> FEATURE:
<223> OTHER INFORMATION: synthesized

<400> SEQUENCE: 105
gtaaaacgac ggccagtgcc aagc                                            24

<210> SEQ ID NO 106
<211> LENGTH: 34
<212> TYPE: DNA
<213> ORGANISM: Artificial Sequence

```
<220> FEATURE:
<223> OTHER INFORMATION: synthesized
<220> FEATURE:
<221> NAME/KEY: misc_feature
<222> LOCATION: 7, 8, 9
<223> OTHER INFORMATION: n = A,T,C or G
<220> FEATURE:
<221> NAME/KEY: misc_feature
<222> LOCATION: 26, 27, 28
<223> OTHER INFORMATION: n = A,T,C or G

<400> SEQUENCE: 106
ggccgcnnna tcgagttttc tcgatnnngc ggcc                                34

<210> SEQ ID NO 107
<211> LENGTH: 7
<212> TYPE: PRT
<213> ORGANISM: Artificial Sequence
<220> FEATURE:
<223> OTHER INFORMATION: synthesized

<400> SEQUENCE: 107

Gln Ser Ser His Leu Val Arg
 1               5

<210> SEQ ID NO 108
<211> LENGTH: 7
<212> TYPE: PRT
<213> ORGANISM: Artificial Sequence
<220> FEATURE:
<223> OTHER INFORMATION: synthesized

<400> SEQUENCE: 108

Gln Ser Ser Asn Leu Val Arg
 1               5

<210> SEQ ID NO 109
<211> LENGTH: 7
<212> TYPE: PRT
<213> ORGANISM: Artificial Sequence
<220> FEATURE:
<223> OTHER INFORMATION: synthesized

<400> SEQUENCE: 109

Asp Pro Gly Ala Leu Arg Val
 1               5

<210> SEQ ID NO 110
<211> LENGTH: 7
<212> TYPE: PRT
<213> ORGANISM: Artificial Sequence
<220> FEATURE:
<223> OTHER INFORMATION: synthesized

<400> SEQUENCE: 110

Arg Ser Asp Asn Leu Val Arg
 1               5

<210> SEQ ID NO 111
<211> LENGTH: 7
<212> TYPE: PRT
<213> ORGANISM: Artificial Sequence
<220> FEATURE:
<223> OTHER INFORMATION: synthesized

<400> SEQUENCE: 111

Gln Ser Gly Asp Leu Arg Arg
 1               5
```

```
<210> SEQ ID NO 112
<211> LENGTH: 7
<212> TYPE: PRT
<213> ORGANISM: Artificial Sequence
<220> FEATURE:
<223> OTHER INFORMATION: synthesized

<400> SEQUENCE: 112

Asp Cys Arg Asp Leu Ala Arg
 1               5

<210> SEQ ID NO 113
<211> LENGTH: 7
<212> TYPE: PRT
<213> ORGANISM: Artificial Sequence
<220> FEATURE:
<223> OTHER INFORMATION: synthesized

<400> SEQUENCE: 113

Arg Arg Ser Ser Cys Arg Lys
 1               5
```